US012579668B2

(12) United States Patent
Molin

(10) Patent No.: US 12,579,668 B2
(45) Date of Patent: Mar. 17, 2026

(54) VIEWER SYSTEMS AND RELATED METHODS WITH MULTI-PIECE REGISTRATION

(71) Applicant: Sectra AB, Linköping (SE)

(72) Inventor: Jesper Molin, Linköping (SE)

(73) Assignee: Sectra AB, Linköping (SE)

( * ) Notice: Subject to any disclaimer, the term of this patent is extended or adjusted under 35 U.S.C. 154(b) by 245 days.

(21) Appl. No.: 18/632,791

(22) Filed: Apr. 11, 2024

(65) Prior Publication Data

US 2024/0420351 A1 Dec. 19, 2024

Related U.S. Application Data

(60) Provisional application No. 63/508,033, filed on Jun. 14, 2023.

(51) Int. Cl.
| | |
|---|---|
| *G06T 7/33* | (2017.01) |
| *A61B 90/00* | (2016.01) |
| *G06F 3/0481* | (2022.01) |
| *G06F 3/04845* | (2022.01) |
| *G06T 7/00* | (2017.01) |

(52) U.S. Cl.
CPC .............. *G06T 7/33* (2017.01); *A61B 90/37* (2016.02); *G06F 3/0481* (2013.01); *G06F 3/04845* (2013.01); *G06T 7/0014* (2013.01); *G06F 2203/04803* (2013.01); *G06T 2200/24* (2013.01); *G06T 2207/10056* (2013.01); *G06T 2207/30024* (2013.01); *G06T 2207/30168* (2013.01)

(58) Field of Classification Search
CPC ....................................... G06T 7/33

USPC ......................................................... 715/799
See application file for complete search history.

(56) References Cited

U.S. PATENT DOCUMENTS

| | | | | |
|---|---|---|---|---|
| 5,975,678 A | * | 11/1999 | Kanematsu | ............ B41J 2/2132 |
| | | | | 358/1.9 |
| 7,599,557 B2 | * | 10/2009 | Koide | ........................ G06T 7/20 |
| | | | | 382/173 |
| 9,412,162 B2 | * | 8/2016 | Molin | ................... G06T 3/4053 |
| 11,963,826 B2 | * | 4/2024 | Kruecker | ............... A61B 5/062 |

(Continued)

OTHER PUBLICATIONS

Fischler , et al., "Random sample consensus: A paradigm for model fitting with applications to image analysis and automated cartography", Communications of the ACM, 24(6):381-395 (Jun. 1981).

(Continued)

*Primary Examiner* — Reza Nabi
(74) *Attorney, Agent, or Firm* — Myers Bigel, P.A.

(57) ABSTRACT

Viewer systems and related methods with user interactive user interfaces that provide a viewport with first and second digital images that allow a user to navigate an active one of the digital images which drives a viewing window over the other digital image to provide a view that moves in response to navigation of the active slide to allow a user to compare and select one of several candidate registrations to register the first and second slides for pathology or other medical review. The user can interact with the user interface to switch which image is the active images (e.g., a WSI or slide image), select an object in the digital image and direct the system to provide other digital images.

24 Claims, 16 Drawing Sheets
(10 of 16 Drawing Sheet(s) Filed in Color)

(56) References Cited

U.S. PATENT DOCUMENTS

| | | | | |
|---|---|---|---|---|
| 2012/0044342 A1* | 2/2012 | Hing | G02B 21/365 | |
| | | | | 348/79 |
| 2013/0162803 A1* | 6/2013 | Steckhan | G02B 21/367 | |
| | | | | 348/79 |
| 2015/0055844 A1* | 2/2015 | Molin | G06T 3/4053 | |
| | | | | 382/131 |
| 2015/0279032 A1* | 10/2015 | Hall | G16H 30/20 | |
| | | | | 382/128 |
| 2018/0088308 A1* | 3/2018 | Liu | G02B 21/367 | |
| 2018/0089496 A1* | 3/2018 | Molin | G06V 20/698 | |
| 2019/0355113 A1* | 11/2019 | Wirch | G06T 7/32 | |
| 2020/0043134 A1* | 2/2020 | Martin | G06T 3/4038 | |
| 2021/0152732 A1* | 5/2021 | Eki | H04N 23/661 | |
| 2023/0089123 A1* | 3/2023 | Lu | A61P 13/00 | |
| | | | | 514/182 |
| 2023/0215052 A1* | 7/2023 | Tang | G06V 10/26 | |
| | | | | 382/133 |
| 2023/0234503 A1* | 7/2023 | Eki | H04N 23/84 | |
| | | | | 348/373 |
| 2023/0315738 A1* | 10/2023 | Srinivasa | G06F 16/2465 | |
| | | | | 707/714 |
| 2024/0020331 A1* | 1/2024 | Schikora | G06V 10/945 | |
| 2024/0153088 A1* | 5/2024 | Danjo | G06T 7/0014 | |
| 2024/0420351 A1* | 12/2024 | Molin | G06F 3/04845 | |

OTHER PUBLICATIONS

Garcia Rojo , et al., "Critical Comparison of 31 Commercially Available Slide Systems in Pathology", International Journal of Surgical Pathology, 14(4):285-305 (2006).

Lotz, Johannes , "Combined local and global image registration and its application to large-scale images in digital pathology", Doctoral dissertation from the Institute of Mathematics and Image Computing of the University of Lübeck (191 pages) submitted 2019, approved for printing May 5, 2020.

Ma , et al., "Image Matching from Handcrafted to Deep Features: A Survey", International Journal of Computer Vision, 129:23-79 (2021).

Mueller , et al., "Real-time deformable registration of multi-modal whole slides for digital pathology", Computerized Medical Imaging and Graphics, 35:542-556 (2011).

Polley, Mei-Yin C., et al., "An International Ki67 Reproducibility Study", Journal of the National Cancer Institute, 105 (24), 2013, 1897-1906.

Sellaro, Tiffany L., et al., "Relationship between magnification and resolution in digital pathology systems", Journal of Pathology Informatics, 4(21), 2013, 5 pages.

Weitz , et al., "The ACROBAT 2022 Challenge: Automatic Registration of Breast Cancer Tissue", Electrical Engineering and Systems Science (Image and Video Processing), arXiv: 2305, 18033, submitted on May 29, 2023.

Extended European Search Report corresponding to European Patent Application No. 24172465.7 (10 pages) (dated Oct. 10, 2024).

* cited by examiner

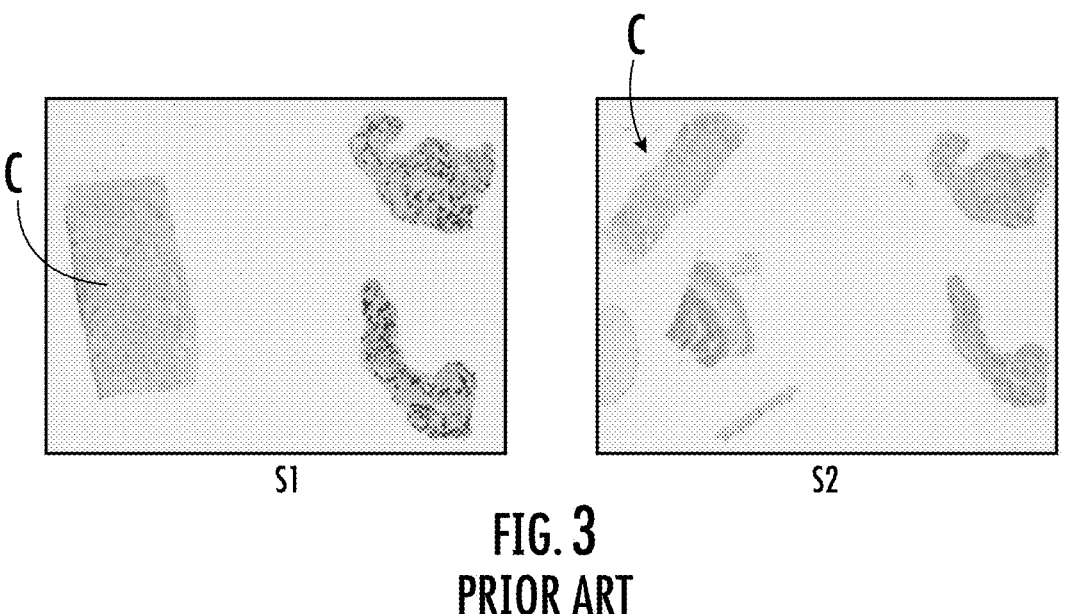
FIG. 3
PRIOR ART
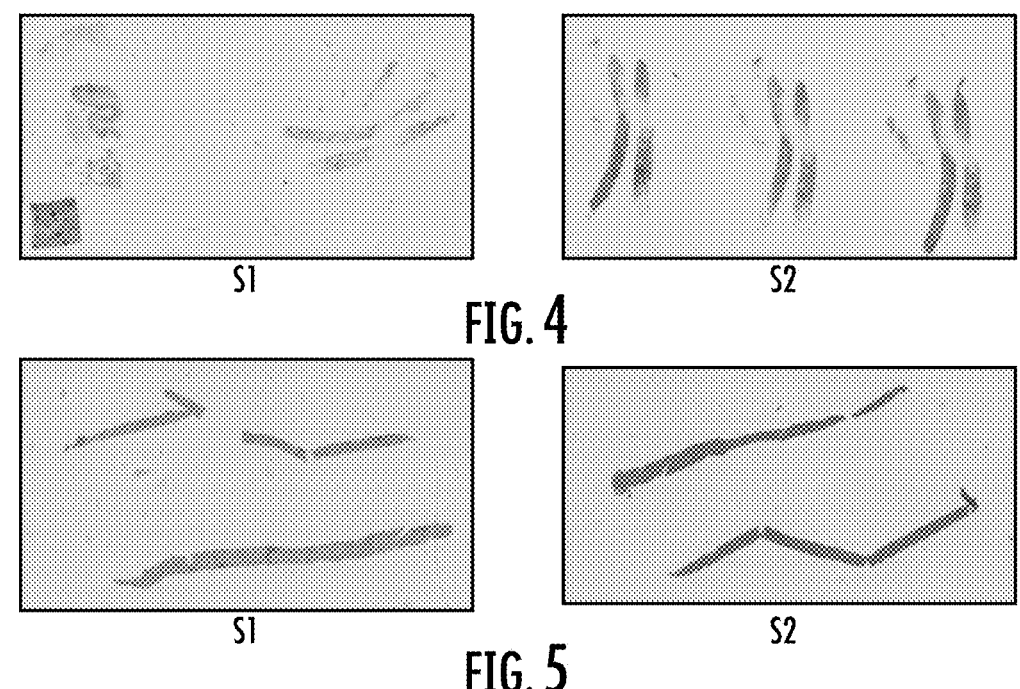
FIG. 4
FIG. 5

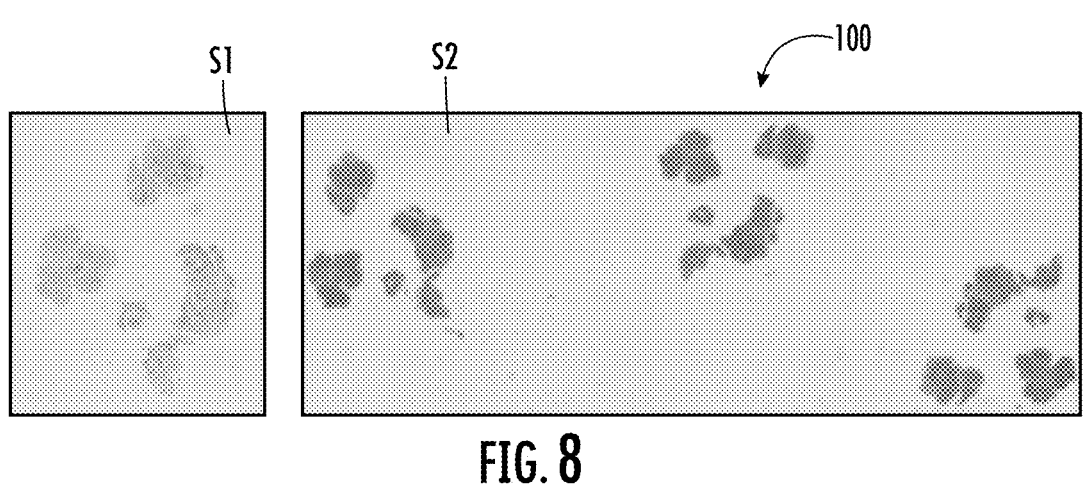
FIG. 8
FIG. 9A
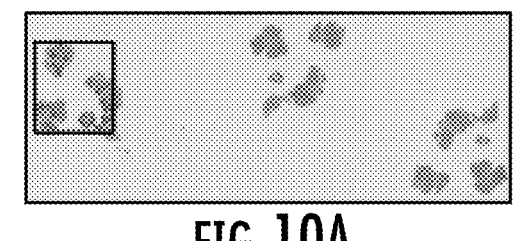
FIG. 10A
FIG. 9B
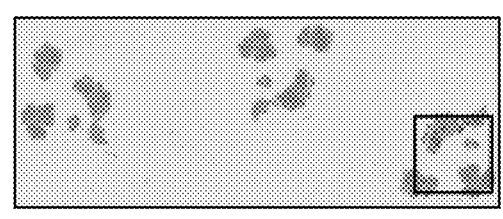
FIG. 10B
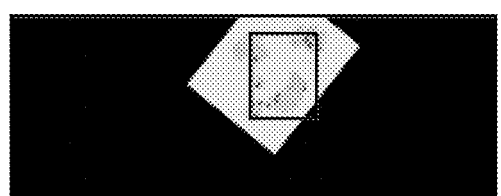
FIG. 9C
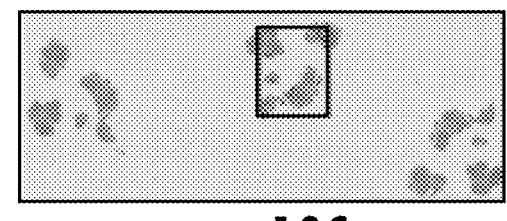
FIG. 10C

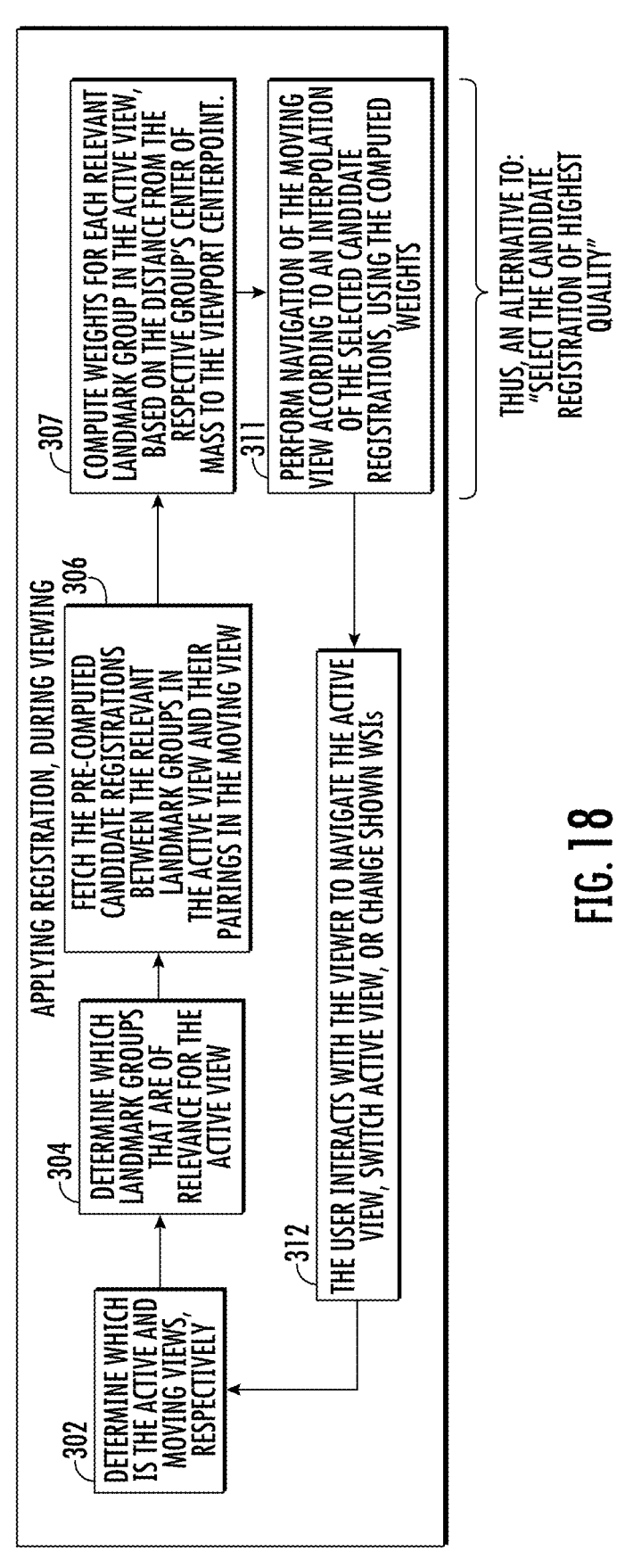

APPLYING REGISTRATION, DURING VIEWING

302 — DETERMINE WHICH IS THE ACTIVE AND MOVING VIEWS, RESPECTIVELY

304 — DETERMINE WHICH LANDMARK GROUPS THAT ARE OF RELEVANCE FOR THE ACTIVE VIEW

306 — FETCH THE PRE-COMPUTED CANDIDATE REGISTRATIONS BETWEEN THE RELEVANT LANDMARK GROUPS IN THE ACTIVE VIEW AND THEIR PAIRINGS IN THE MOVING VIEW

307 — COMPUTE WEIGHTS FOR EACH RELEVANT LANDMARK GROUP IN THE ACTIVE VIEW, BASED ON THE DISTANCE FROM THE RESPECTIVE GROUP'S CENTER OF MASS TO THE VIEWPORT CENTERPOINT.

311 — PERFORM NAVIGATION OF THE MOVING VIEW ACCORDING TO AN INTERPOLATION OF THE SELECTED CANDIDATE REGISTRATIONS, USING THE COMPUTED WEIGHTS

312 — THE USER INTERACTS WITH THE VIEWER TO NAVIGATE THE ACTIVE VIEW, SWITCH ACTIVE VIEW, OR CHANGE SHOWN WSIs

THUS, AN ALTERNATIVE TO: "SELECT THE CANDIDATE REGISTRATION OF HIGHEST QUALITY"

FIG. 18

VIEWER SYSTEMS AND RELATED METHODS WITH MULTI-PIECE REGISTRATION

RELATED APPLICATIONS

This patent application claims the benefit of and priority to U.S. Provisional Application Ser. No. 63/508,033, filed Jun. 14, 2023, the contents of which are hereby incorporated by reference as if recited in full herein.

FIELD OF THE INVENTION

The present invention is particularly suitable for medical microscopy within the digital pathology domain, such as image processing for Whole-Slide Imaging (WSI).

BACKGROUND

A pathologist's analysis of histology images is primarily subjective. Since health care practice is evidence-based, it is crucial to have reproducible methods. The subjective nature of many diagnostic tasks in anatomic pathology and cytology is, however, known to cause reproducibility problems, i.e., high inter- and intra-observer variability in many diagnostic situations. See, Polley et al., An International Ki67 Reproducibility Study. JNCI Journal of the National Cancer Institute 105.24 (2013):1897-1906. PMC. Web. 24 Nov. 2015.

Today there are many scanners capable of producing high-quality digital images from the microscopy glasses. The resulting images are very large, often 100,000×200,000 pixels. See, e.g., Rojo et al., Critical comparison of 31 commercially available slide systems in pathology, Int J Surg. Pathol., 2006; 14(4):285-305. This digital practice is often called "WSI" or "virtual microscopy" for cytopathology. The resulting digital images can be very large, for instance 30,000×40,000 pixels, 100,000×100,000 pixels or more. In histology, a two-dimensional (2D) image often suffices, but there is also the possibility to produce slices across the depth of the tissue section, creating a three-dimensional (3D) dataset even though the extent in the z direction can be far different from the x-y directions.

During review of pathology images, it is common practice to create multiple slides from the tissue block. The slides are often stained using different stainings that highlight different parts of the tissue as can be seen in FIG. 1. In this example, two pathology slides with different stainings are shown, slide 1 (S1) to the left H&E and slide 2 (S2) to the right Estrogen IHC of a breast cancer.

The pathologist often wants to quickly compare slides with different stainings with each other at high magnification in a side-by-side view, where the same tissue compartment can be seen with the different stainings. A common mode in pathology viewers is that these side-by-side views can be linked, such that any pan-zoom navigation in the first slide is automatically applied on the second slide, resulting in that both views always show the same tissue location.

To achieve this, an image registration algorithm can be used that disregards image features specific to the staining, such as the color channels. The user selects to two slides, the registration is applied, and the region can be showed in a pathology viewer with a single click as seen in FIG. 2 where two slides, S1, S2 are shown side-by-side in a prior art pathology viewer.

However, in practice, this is less straight forward than one might think since slides can often have non-trivial composition. One complication is that there may be several tissue sections on each slide, where each section is a potential registration target to all sections in the other slide as seen in FIG. 4. Another complication is that parts of a tissue section may be dislocated as seen in FIG. 5.

Yet another complication is that stained slides other than H&E often contain a control piece used to check the staining quality that has nothing to do with the piece under investigation. It is very hard for an algorithm to know which piece is the right one since the control piece C is usually just a piece from another case that has been successfully stained before as the pieces to the left of each slide S1, S2 in FIG. 3. See, Weitz et al., The Acrobat 2022 Challenge: Automatic Registration of Breast Cancer Tissue, Electrical Engineering and Systems Science (Image and Video Processing), arXiv: 2305, 18033, submitted on May 29, 2023, discussing WSI registration methods and the criticality of alignment of tissue between histopathological whole-slide-images (WSI).

Thus, there remains a need for improved image analysis methods and viewer systems that can provide a more robust registration protocol.

SUMMARY

Embodiments of the invention provide viewers, methods and/or image processing circuits that allow user interactions to provide a semi-automated image registration process of WSI images.

Embodiments of the invention are directed to viewer systems and methods of processing digital pathology and cytology images for viewing.

Embodiments of the invention are directed to methods of registering medical images for viewing. The methods include: electronically providing a database of candidate registrations of a plurality of different medical images for respective patients. A pair of the different medical images of a single patient of the plurality of different medical images has multiple candidate registrations in the database of candidate registrations and multiple image regions of a first medical image of the pair of the different medical images are each related to an image region in a second medical image of the pair of different medical images through at least one candidate registration in the database of candidate registrations. The methods also include electronically providing a viewer comprising a first window with a first viewing window user interface and a second window with a second viewing window user interface; displaying a viewport of the first medical image in the first window; displaying a viewport of the second medical image in the second window; accepting user input of a user to select one of the first window or the second window to be an active window for user navigation and which makes a non-selected other of the first window or the second window a non-active, follower window; obtaining candidate registrations from the database of candidate registrations that are related to the first medical image or the second medical image in the active window; and electronically automatically selecting a registration from the obtained candidate registrations based on proximity of the image region of the obtained candidate registrations to the viewport of the active window.

Each image region can be an area that is defined by a respective keypoint cluster.

Each candidate registration in the database of candidate registrations can have a candidate registration quality measure. The electronically automatically selecting a registration from the obtained candidate registrations can also be based on the candidate registration quality measure.

The candidate registrations in the database of candidate registrations can be computed through keypoint pairing of pairs of first and second keypoint clusters with a first keypoint cluster in the first medical image and a second keypoint cluster in the second medical image with the keypoint clusters represent respective image regions in the first and second medical images.

The candidate registration quality measure can be calculated based, at least in part, by a number of keypoints in a respective keypoint cluster, with keypoint clusters having a greatest number correlated to a greater registration quality measure.

The selecting can include determining viewport proximity of the first or second viewport that is the active window to a midpoint of keypoint clusters connected to the candidate registrations.

The method can include automatically electronically moving the viewport of the follower window according to the selected registration whereby the viewport of the first medical image and the viewport of the second medical display respective, corresponding image portions of the first and second medical images.

The method can include changing the viewport of the active window as directed by the user in a user interface of the active viewing window to navigate about image regions in the active window; then, in response to change of the viewport of the active window, automatically electronically moving the viewport of the follower window, synchronized to follow movement of the viewport of the active window.

The method can include accepting user input to change the viewport of the active window and automatically electronically repeating the selecting registration step and automatically moving the viewport of the follower window according to the change in the viewport of the active window.

The method can include changing one or more selected registrations from the obtained candidate registrations whereby different objects in the image region of the active window becomes aligned with a common (the same) region in the image region of the follower window.

The medical images can be digital pathology slide images of a tissue block of the single patient.

Keypoints of spaced apart objects in different image regions are used to identify similar objects in the different medical images to identify candidate registrations for the obtaining step.

Each candidate registration can be electronically connected to a corresponding plurality of keypoints with increasing numbers of keypoints corresponding to higher quality candidate registration quality measures.

The method can include electronically determining if there are candidate registrations that have an image region overlapping with the viewport in the active window and accepting user input via a single user interface action, whereby each single user interface action executes selection of another candidate registration in the order of decreasing candidate registration quality measure.

A sequence of selecting candidate registrations in response to respective single user interface actions can be ordered according to spatial location of the image region of the non-active window with the image region of the candidate registrations.

The selecting the registration can be carried out, at least in part, by selecting a plurality of different candidate registrations from the obtained candidate registrations corresponding to a current position of the active image viewport, each of the selected plurality of candidate registrations corresponds to a different relevant image region in the active image.

Each of the selected plurality of candidate registrations can have a weighting used for the candidate registration quality measure, and the weighting can be based on a distance from a center of mass of an active image keypoint cluster in a respective selected candidate registration to a centerpoint of the active image viewport.

The medical images can be two-dimensional (2-D) WSI images having between about $1\times10^6$ pixels to about $1\times10^{12}$ pixels.

The medical images can be three-dimensional (3-D) WSI images, and a z extent can have a plurality of slices across a depth of a tissue section with less pixels in the z extent relative to x and y extents.

Other embodiments are directed to viewer systems for evaluating Whole Slide Images (WSI). The viewer systems include: a display; and a circuit in communication with the display, the circuit comprising at least one processor that:

provides or in communication with a database of candidate registrations of a plurality of different medical images for respective patients, wherein a pair of the different medical images of a single patient of the plurality of different medical images has multiple candidate registrations in the database of candidate registrations, wherein each region of multiple regions of a first medical image of the pair of the different medical images is related to a region in a second medical image of the pair of different medical images through at least one candidate registration in the database of candidate registrations;

provides a viewer comprising a first window and a second window;

displays a viewport of the first medical image in the first window;

displays a viewport of the second medical image in the second window;

accepts user input of a user to select one of the first window or the second window to be an active window for user navigation and which makes a non-selected other of the first window or the second window a non-active, follower window;

obtains candidate registrations from the database of candidate registrations that are related to the first medical image or the second medical image in the active window; and selects a registration from the obtained candidate registrations based on proximity of the image region of the obtained candidate registration to the viewport of the active window.

An image region can be associated with an area spanned by keypoint clusters.

Each candidate registration in the database of candidate registrations can have a candidate registration quality measure.

The candidate registrations in the database of candidate registrations can be computed through keypoint pairing of pairs of first and second keypoint clusters, the first keypoint cluster in the first medical image and the second keypoint cluster in the second medical image, and wherein the keypoint clusters represent respective image regions in the first and second medical images.

The candidate registration quality measure, where used, can be calculated based, at least in part, by a number of keypoints in a respective keypoint cluster, with keypoint clusters having a greatest number correlated to a greater registration quality measure.

The at least one processor can be configured to select the registration by determining viewport proximity of the first or second viewport that is the active window to a midpoint of keypoint clusters connected to the candidate registrations.

The at least one processor can be configured to automatically move the viewport of the follower window according to the selected registration whereby the viewport of the first medical image and the viewport of the second medical display respective, corresponding image portions of the first and second medical images.

The at least one processor can be further configured to: change the viewport of the active window as directed by the user in a user interface of the active viewing window to navigate about image regions in the active window; then, in response to change of the viewport of the active window, automatically move the viewport of the follower window, synchronized to follow movement of the viewport of the active window.

The circuit can be configured to accept user input to change the viewport of the active window whereby the at least one processor then automatically selects another candidate registration as a current selected registration and moves the viewport of the follower window according to the change in the viewport.

The at least one processor can be further configured to change selected registrations from the obtained candidate registrations whereby different objects in the image region of the active window become aligned with the same region in the image region of the follower window.

The medical images can be digital pathology slide images of a tissue block of the single patient.

The at least one processor can be configured so that keypoints of spaced apart objects in different image regions identify similar objects in the different medical images to identify obtained candidate registrations.

Each candidate registration can be electronically connected to a corresponding plurality of keypoints with increasing numbers of keypoints corresponding to higher quality candidate registration measures.

The at least one processor can be configured to: determine if there are candidate registrations that have an image region overlapping with the viewport in the active window; and accept user input via a single user interface action, where each action executes selection of another candidate registration in the order of decreasing candidate registration quality measure.

The at least one processor can be configured to provide a sequence of selecting candidate registrations in response to user action that is ordered according to spatial location of the image region of the non-active window with the image region of the candidate registrations.

The selected registration can be selected, at least in part, by selecting a plurality of candidate registrations corresponding to a position of the active image viewport, each selected plurality of candidate registrations corresponds to a different relevant image region in the active image.

Each of the selected plurality of candidate registrations can have a weighting used for the candidate registration quality measure, and the weighting can be based on a distance from a center of mass of an active image keypoint cluster in a respective selected candidate registration to centerpoint of the active image viewport.

The medical images can be two-dimensional (2-D) WSI images having between about $1\times10^6$ pixels to about $1\times10^{12}$ pixels.

The medical images can be three-dimensional (3-D) WSI images and can have a z extent with a plurality of slices across a depth of a tissue section with less pixels in the z extent relative to x and y extents.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is an example of different control pieces for two different slides of tissue slides.

FIG. 4 are images of multiple sections of tissue placed on a single glass slide (right image) making it possible to register the slides in three different ways (left side image).

FIG. 5 are images showing how parts of tissue sections, in this case biopsies, can migrate and dislocate. The bottom biopsy in the left slide and the top biopsy in the right slide approximately correspond to the shape of the original tissue, whereas tissue pieces have dislocated in the two other biopsies.

FIG. 6A shows pen-markings on the slide; FIG. 6B shows an edge of a cover in a middle of tissue, offset from a slide edge; FIG. 6C shows weak staining/low contrast; and FIG. 6D shows a dirty slide.

FIG. 8 shows a pair of slide images of tissue samples.

FIGS. 9A-9C show three candidate registrations on the first slide of the two slides shown in FIG. 8 in order of quality (number of key points in the pair).

FIGS. 10A-10C are images that show corresponding registration candidates to FIGS. 9A-9C for the second slide of the two slides shown in FIG. 8.

FIG. 18 is a flow chart of actions that allow several active groups for applying registration during viewing provided by a viewer according to embodiments of the present invention.

DETAILED DESCRIPTION

Figures 1, 2:
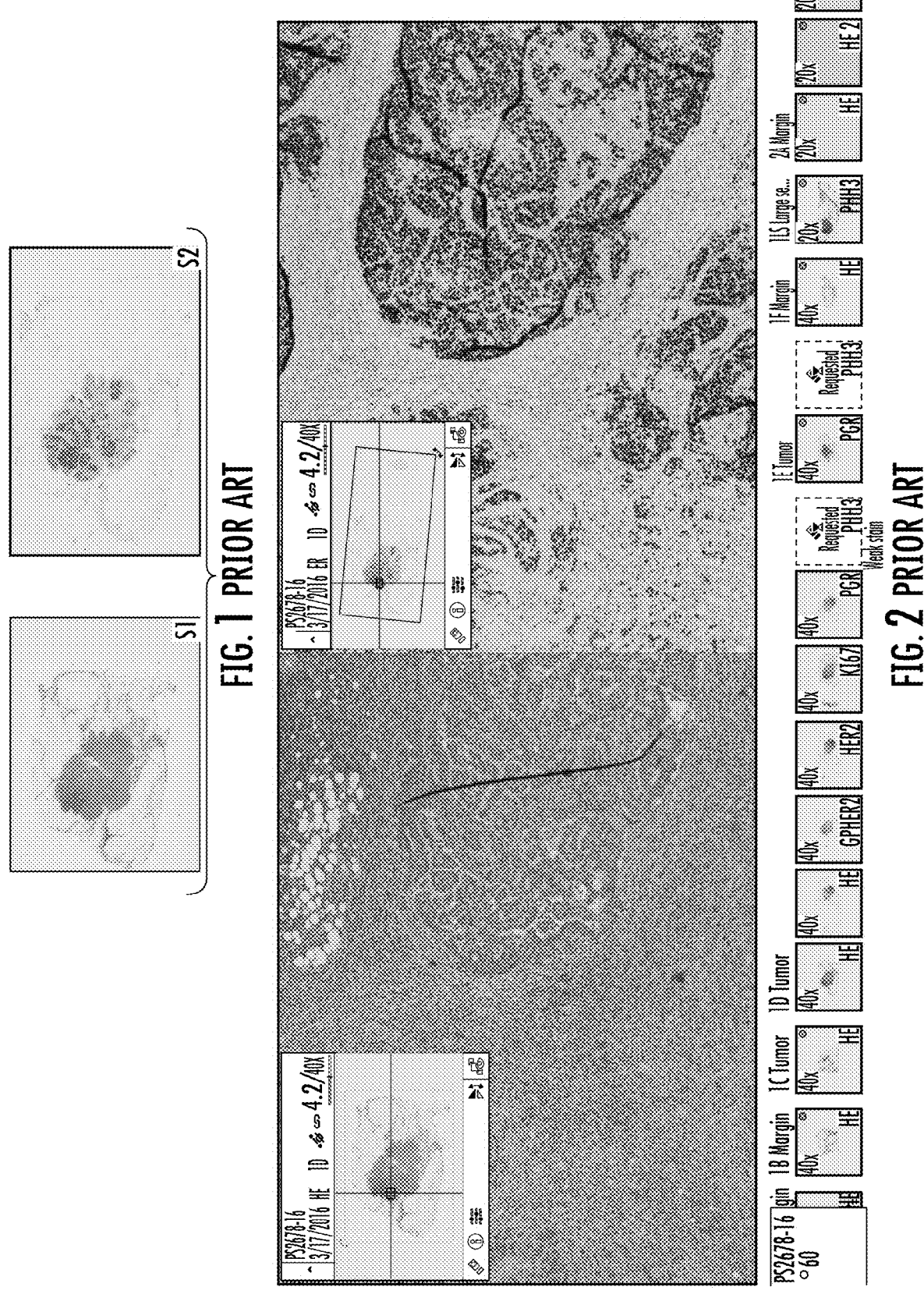
FIG. 1 shows two digital pathology slides with different staining, H&E (left) and Estrogen 1HC (right) of a breast cancer.
FIG. 2 is an example display of two slides shown side by side by a prior art pathology viewer.

The present invention will now be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. The term "Fig." (whether in all capital letters or not) is used interchangeably with the word "Figure" as an abbreviation thereof in the specification and drawings. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the thickness of certain lines, layers, components, elements or features may be exaggerated for clarity. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. The phrase "in communication with" refers to direct and indirect communication. Although described or shown with respect to one embodiment, the features so described or shown can apply to other embodiments.

The term "circuit" refers to software embodiments or embodiments combining software and hardware aspects, features and/or components, including, for example, at least one processor and software associated therewith embedded therein and/or executable by and/or one or more Application Specific Integrated Circuits (ASICs), for programmatically directing and/or performing certain described actions, operations or method steps. The circuit can reside in one location or multiple locations, it may be integrated into one component or may be distributed, e.g., it may reside entirely in a workstation or single computer, partially in one workstation, cabinet, computer, or server and/or totally in a remote location away from a local display at a workstation. The circuit can communicate with a local display, computer and/or processor, over a LAN, WAN and/or internet to transmit WSI images and/or perform the patch gallery user interaction of a viewer.

The term "automatically" means that the operation can be substantially, and typically entirely, carried out without human or manual input, and is typically programmatically directed and/or carried out. The terms "semi-automatically" and "semi-automatic" means that user input is required to carry out one or more operation/action for the process.

The term "electronically" includes both wireless and wired connections between components.

The term "programmatically" means that the operation or step can be directed and/or carried out by a digital signal processor and/or computer program code. Similarly, the term "electronically" means that the step or operation can be carried out in an automated manner using electronic components rather than manually or using merely mental steps.

The term "clinician" refers to a pathologist, physician, oncologist, or other personnel desiring to review medical data of a subject, which is typically a live human or animal patient, but forensic uses are also contemplated.

The term "user" refers to a person, or device associated with that person, that uses the noted feature or component, such as a technician, pathologist or other expert, clinician or patient.

The term "about" means that the recited parameter can vary from the noted value, typically by +/−20%.

The term "PACS" refers to PICTURE ARCHIVING AND COMMUNICATION SYSTEM.

The term "magnification" means the image resolution measured in micrometers per pixel, applicable both for the scanned image and the images displayed on screen. Higher magnification corresponds to a lower micrometer per pixel value than lower magnification and vice versa.

The term "high magnification" means displaying an image with an on-screen magnification relatively close to the magnification with which the original image was scanned. Recent (2013) clinical scanning protocols commonly employ 200 times or 400 times magnification, corresponding to 0.5 and 0.25 micrometers per pixel respectively. In this case, "high magnification" corresponds to a magnification range of between about 0.1 micrometers (i.e., microns) to about 1 micron per pixel, more typically between about 0.1 micron to about 0.5 micron per pixel.

The term "low magnification" means displaying an image with an on-screen magnification substantially lower than the magnification with which the original image was scanned. In the case of using a scanning protocol of 0.5 or 0.25 micrometers per pixel, "low magnification" corresponds to magnification range of about 2 micrometers per pixel and above, for example about 10 micrometers per pixel.

The zoom letter "×" indicates a mathematical ("times") multiplier factor associated with a magnification level indicated by the adjacent number, e.g., 0.1×, 1×, 1.25×, 10× and the like, which means that the zoom view is shown at the noted magnification level relative to the original image. Thus, the 1×, 10× and the like descriptors for the digital image refer to the "true optical magnification" of the objective inside the slide scanner. These measures are intended to relate to the visual experience of using the 1×, 10×, etc., objective in a microscope. However, the perceived resolution also depends on other factors: the sensor pixel size, the monitor resolution and the viewing distance. See, e.g., Sellaro et al., Relationship between magnification and resolution in digital pathology systems, J Pathol Inform 2013; 4:21, the contents of which are hereby incorporated by reference as if recited in full herein. The "microns per pixel" definition refers to the digital image itself (not monitor resolution and viewing distance that may vary). To be clear, a certain micron per pixel number is not exactly coupled to a magnification factor such as 10× as the viewers can be used for various different systems and laboratories. However, these magnification levels are used as a shorthand herein, e.g., so as to refer to a certain micron value per pixel, so that, for example, 10× is a convenient shorthand for a digital image with a resolution of approximately 1 micron per pixel. The magnification level is decoupled from the resolution in which the digital image was acquired, for example, an image acquired at 40× can be displayed at the zoom level of 10×. See, U.S. Pat. No. 9,412,162 for further details of zoom-to-view magnification viewing methods, the contents of which are hereby incorporated by reference as if recited in full herein.

The digital images can be medical images of a patient.

The medical images can be digital images of a glass (or other suitable substrate) WSI of a slide of a tissue sample depicted by a medical microscope. The digital images can be high resolution and have between about $1\times10^3$-$1\times10^{12}$ pixels and a magnification typically about 0.1-1 micron per pixel, more typically between about 0.1-0.5 micrometers per pixel.

The viewer can provide a first medical image, e.g., a first digital WSI image, and a second medical image, e.g., a second digital WSI image, side-by-side, corresponding to respective two separate slides from a common tissue block of a single patient.

The term "viewer" refers to an electronic interface that allows a user to interact with a display to evaluate tissue samples associated with digital medical images such as slide images, WSI. The terms "digital image of a slide" and "slide image" and derivatives thereof are used interchangeably herein.

The term "viewport" refers to the area of a digital image that is shown in a viewer window. In pathology, the viewport is often much smaller than the full slide due to the need to zoom in to details in the image.

The term "real time" means there is 50 milliseconds or less latency between successive views provided by a viewer to provide different candidate registrations in response to user input.

The term "original" image refers to a source digital image from a digital scanner that has not been image processed to alter features for enhancement.

The viewer can have a semi-automatic registration process that provides a user interface that is configured to with an image processing system, method, module or circuit that employs user (e.g., pathologist) input to navigate an active view, switch an active view or change what digital WSI image is shown in a current view of the viewer to thereby identify a candidate registration as a "best" registration.

As will be discussed further below, the term "keypoint groups" refers to a set of identified points (keypoints) of a respective feature, object, or part of object in a digital medical image such as a digital pathology or cytology slide, WSI.

Generally stated, embodiments of the present invention provide a solution that reformulates the problem from trying to match two images automatically to trying to find all possible registration candidates and using the user context to filter out which registration to use. This approach can provide a more robust protocol for handling messy slides found in clinical practice.

Referring to FIG. 4, another complicating factor for automated registration is that multiple slides from the same tissue can be placed on the same slide so there is not a single way that two slides can register together. As shown in FIG. 4, there are three different ways that the left slide (S1) can be registered with the right slide (S2).

In addition, pieces of tissue can also break off and move from an original position and move around, as shown between slides S1 and S2 in FIG. 5. In S1, a piece of the tissue in the top biopsy of slide S1 has migrated relative to its corresponding biopsy in slide S2, and the bottom biopsy of slide S2 has broken into three pieces compared to the intact corresponding biopsy of slide S1.

Figures 6A, 6B, 6C, 6D:
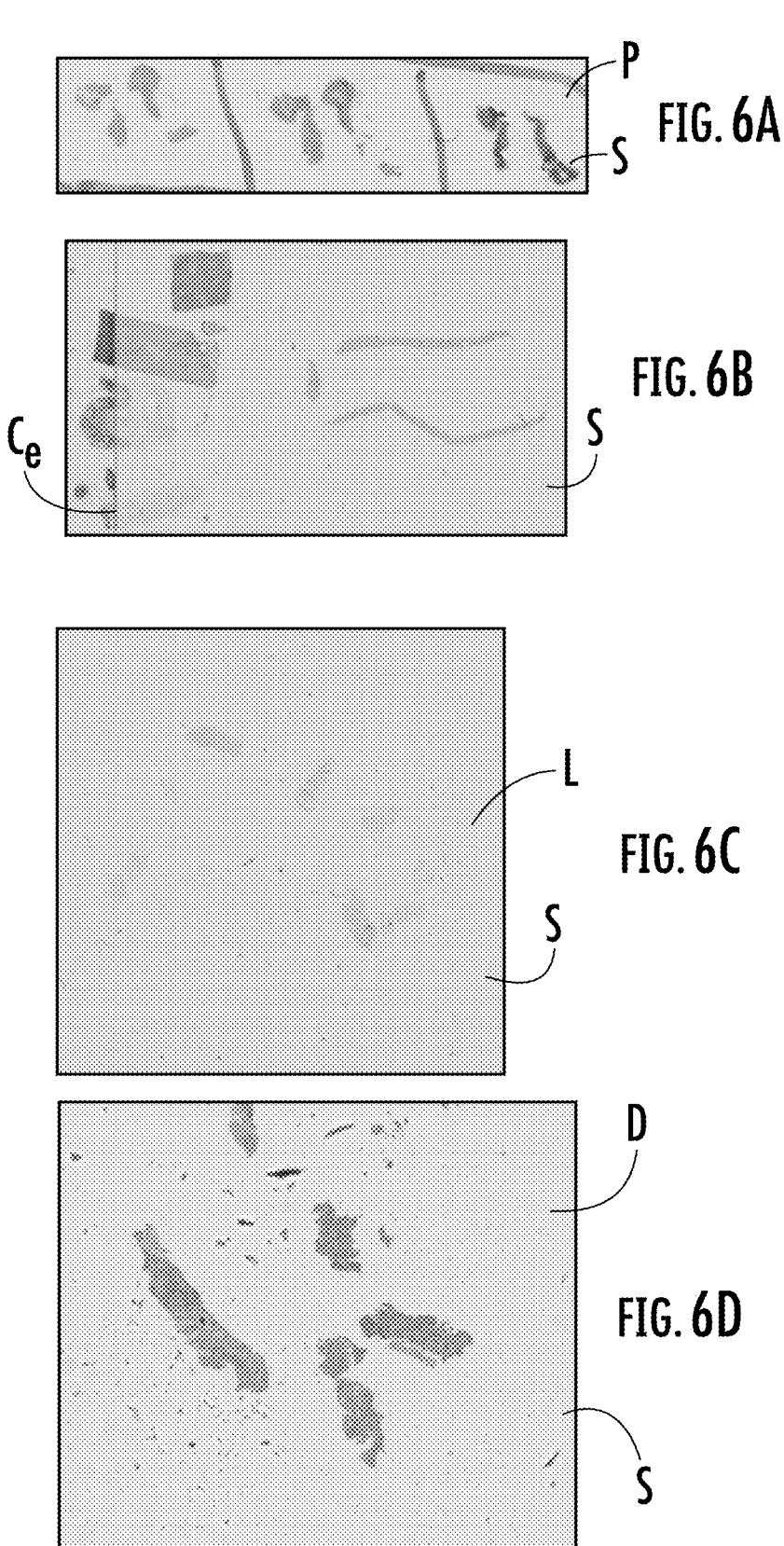
FIGS. 6A-6D are digital WSI of various artifacts that can complicate a registration process.

Another complicating factor is that various other artifacts can be present on the slides S making registration difficult. FIG. 6A shows pen-markings P on the slide S. FIG. 6B shows an edge of the cover class Ce in the middle of the tissue of a respective slide S. FIG. 6C shows weak staining causing low contrast L for the slide S. FIG. 6D shows a dirty slide S with dirt D present on the slide S.

Once two matching pieces are identified between slides S, the registration can be straight forward. However, the best way to match tissue objects and/or pieces so that registration is correct given the above complicating factors is a problem addressed by embodiments of the present invention.

In the past, some systems identified a biggest block of tissue on the slides which was used to register them together. The picked registration was then used as a global registration of the whole slide. This protocol worked well for a surgical specimen because then the piece of interest is often bigger than the control piece. Picking the largest piece also filters out most artifacts since artifact objects in the image tend consist of many small pieces. This was combined with a strict rejection algorithm, measuring how good the match was and rejecting anything that was slightly off, leaving the user to then manually register slides instead.

In the literature there are two types of solutions of registrations, the first solution is to use global non-rigid registration in low resolution that is pre-processed and then a local rigid registration around the area that is visualized in the viewer. Such a method is described e.g., by D. Mueller et al., "Real-time deformable registration of multi-modal whole slides for digital pathology," Computerized Medical Imaging and Graphics, vol. 35, no. 7-8, pp. 542-556, October 2011, doi:10.1016/j.compmedimag.2011.06.006. The content of this document is hereby incorporated by reference as if recited in full herein.

This approach handles smaller deformations such as the pieces moving around a small amount. However, this approach will have problems with the scenarios described in FIGS. 4-6 since the non-rigid registration algorithm is not flexible enough to handle large deformations, or non-matching or foreign objects in the image. It is also difficult for systems using this approach to perform in real time since a registration algorithm needs to be running during navigation in the image.

The other solution found in the literature is to avoid the problem altogether by using curated datasets with strictly using one section per slide. The existing literature is very focused on achieving cell-level accuracy, and the registration error is measured in how well aligned the images are on a pixel level. However, this excludes the majority of cases in clinical routine. For a review of the registration algorithms in digital pathology, the PhD thesis of Johannes Lotz is recommended. Lotz, J. (2020). Combined local and global image registration and its application to large-scale images in digital pathology. Doctoral dissertation. DOI:10.24406/mevis-n-638730. The content of this document is hereby incorporated by reference as if recited in full herein. See also, Weitz et al., The Acrobat 2022 Challenge: Automatic Registration of Breast Cancer Tissue, Electrical Engineering and Systems Science (Image and Video Processing), arXiv: 2305, 18033, submitted on May 29, 2023, discussing WSI registration methods and the criticality of alignment of tissue between histopathological whole-slide-images (WSI), the contents of which are hereby incorporated by reference as if recited in full herein.

It is not believed that a study identifying the problem or any solution for messy slides has been made and this problem is likely considered very hard to solve algorithmically.

Embodiments of the present invention can provide image processing systems that avoid a registration algorithm or process that automatically assumes and takes decisions like: is this one piece of tissue or two pieces of tissue? Is this a control piece or a tissue under investigation? These decisions are very hard to automate, so by deriving these as late as possible and based on user input per embodiments of the present invention, the problem can be avoided.

Embodiments of the present invention can electronically review digital images of slides (e.g., WSI) of tissue sections from one tissue block and find all possible objects and for each object identify all candidate registrations to other digital images of slides. During viewing, a viewer provides a viewport with a first digital medical image and a second digital medical image of a patient. One of the first and second digital images is an active image allowing user navigation and the other is a follower image which can be described as a "moving image" as a viewing window moves in response to interactions with the active image. The user's viewport on the follower image is used to select which is the object of interest, such as a closest object. A best registration to the follower image can be one that has the selected closest object is used to automatically transform the moving image in real time.

Embodiments of the present invention can provide a viewport that provides a viewing window showing a medical image, e.g., slide S1 or S2, and the viewport also defines which extent of the medical image that is displayed. The registration methods of the present invention relate to the situation when there are at least two viewports simultaneously displayed.

The candidate registration selection can be based on the viewport position (i.e., by user interaction but without extra user actions relative to conventional viewers) on a non-active image.

The moving image with the candidate registration can be updated and/or repeated every time the viewport moves on the fixed image and can be performed extremely quickly, without any problem in under about 50 ms, or even 5 ms or less. The viewer systems may operate at frequency of about 120 Hz.

Referring to FIGS. 8, for a pair of images S1, S2, three candidate registrations are possible based on slide 2, FIGS. 10A-10C. The candidate registrations (FIGS. 9A-9C) can be identified or found in order of quality or match. Note that FIGS. 9A-C shows image S1 translated and rotated according to the three possible registrations (FIGS. 10A-C, respectively), to different areas of image S2. In this example, a number of keypoints are matching between the image in Slide S1 and a candidate registration in Slide S2, e.g., in the slide pair.

All possible candidate registrations can be provided to or accessed by a viewer 100 (FIGS. 12-14) when a user wants to compare two digital medical images such as two slide images S1, S2. In the following description, the viewer is assumed to have been set in a mode where several images are shown and where the navigation of the respective viewports are linked. A pathology viewer would typically have the capability to run also without this linked view mode, where switching between modes is controlled by the user.

The viewer 100 (FIG. 8, 12) can be constructed in such a way that only one image S1 or S2 is the active image at any one time. The active image is the image S1, S2 where the user last navigated in, using the UI, such as a mouse or can be selected by a UI to be the "active image" 25a for navigation. In this embodiment, the other image is not used for navigation and can be referred to as a "non-active image" 25n. However, the view of the non-active image 25n will change in response to the navigation of the active image 25a. The active image 25a also allows a user to navigate to different magnifications and positions and the viewports are updated to show corresponding locations of tissue.

For example, if the left image S1 is the active image, the first candidate registration (FIGS. 9A, 10A) will be used by default, and then the user can provide an input, e.g., press <space>, to switch between all possible registrations (FIGS. 9A-9C) which would cause the view of S1 to remain fixed while the view of S2 is translated and rotated such that the tissue section groups of FIGS. 10A-C, respectively, are aligned with the tissue section group of S1.

If the right image S2 is the active image 25a, the candidate registration that is closest to the middle point of the viewport of slide S2, of the viewer 100 is first selected, e.g., corresponding to FIGS. 9A and 10A. When the user navigates slide S2 in the active image 25a such that the viewport middle point is closer to another candidate registration, such as one of those depicted in FIGS. 10B or 10C, that closest candidate registration will be selected. In this case with three areas of S2 each having a candidate registration with the same area of S1, the effect is that a target area in the non-active image 25n will be shown again and again independent of what section the user is looking at in the active image 25a as will be discussed further below.

Figure 12:
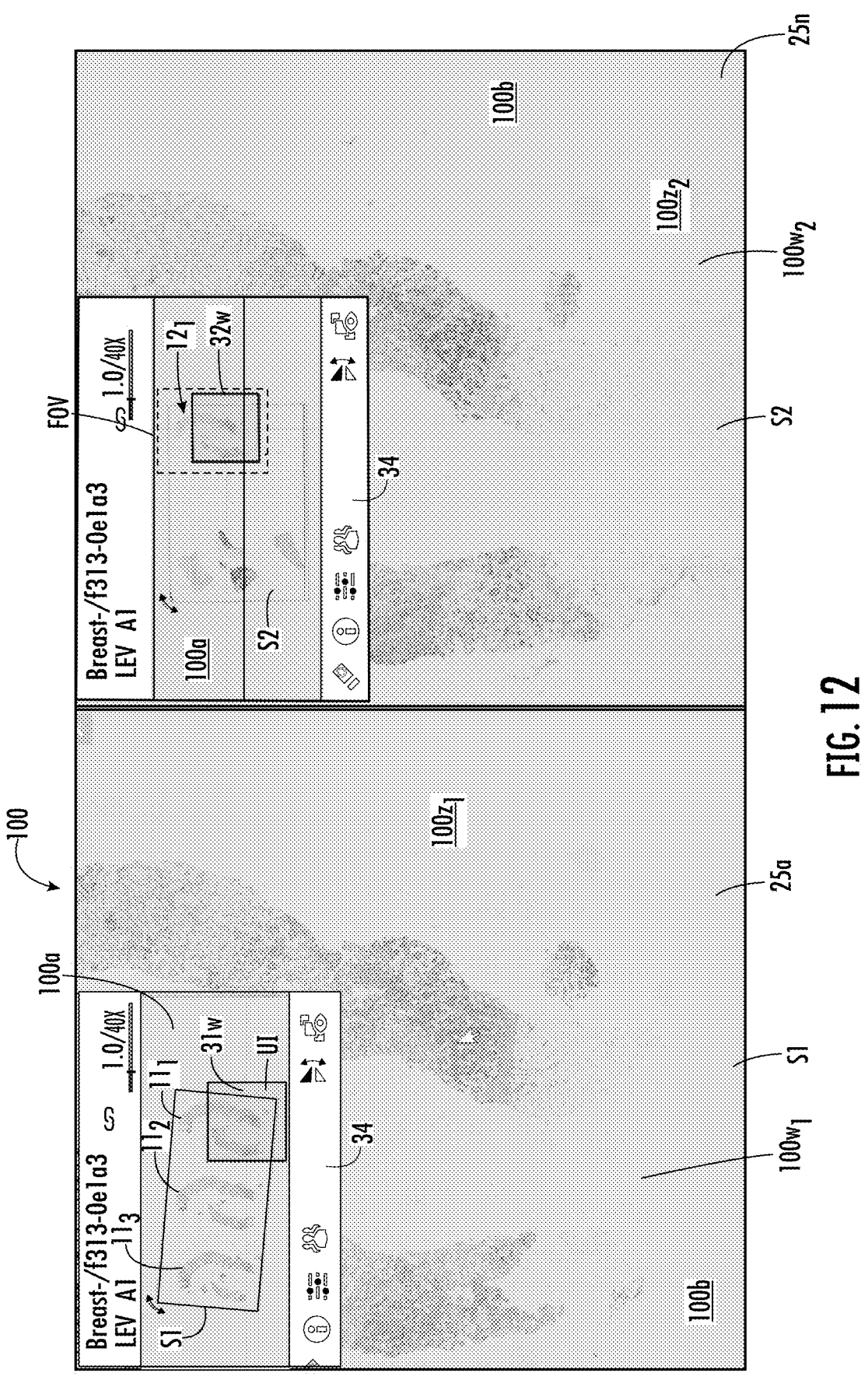
FIGS. 12-14 are a sequence of images of a display provided by a user interactive viewer with two images, one being an active image that allows a user to review candidate registrations based on the active image according to embodiments of the present invention.
Figure 13:
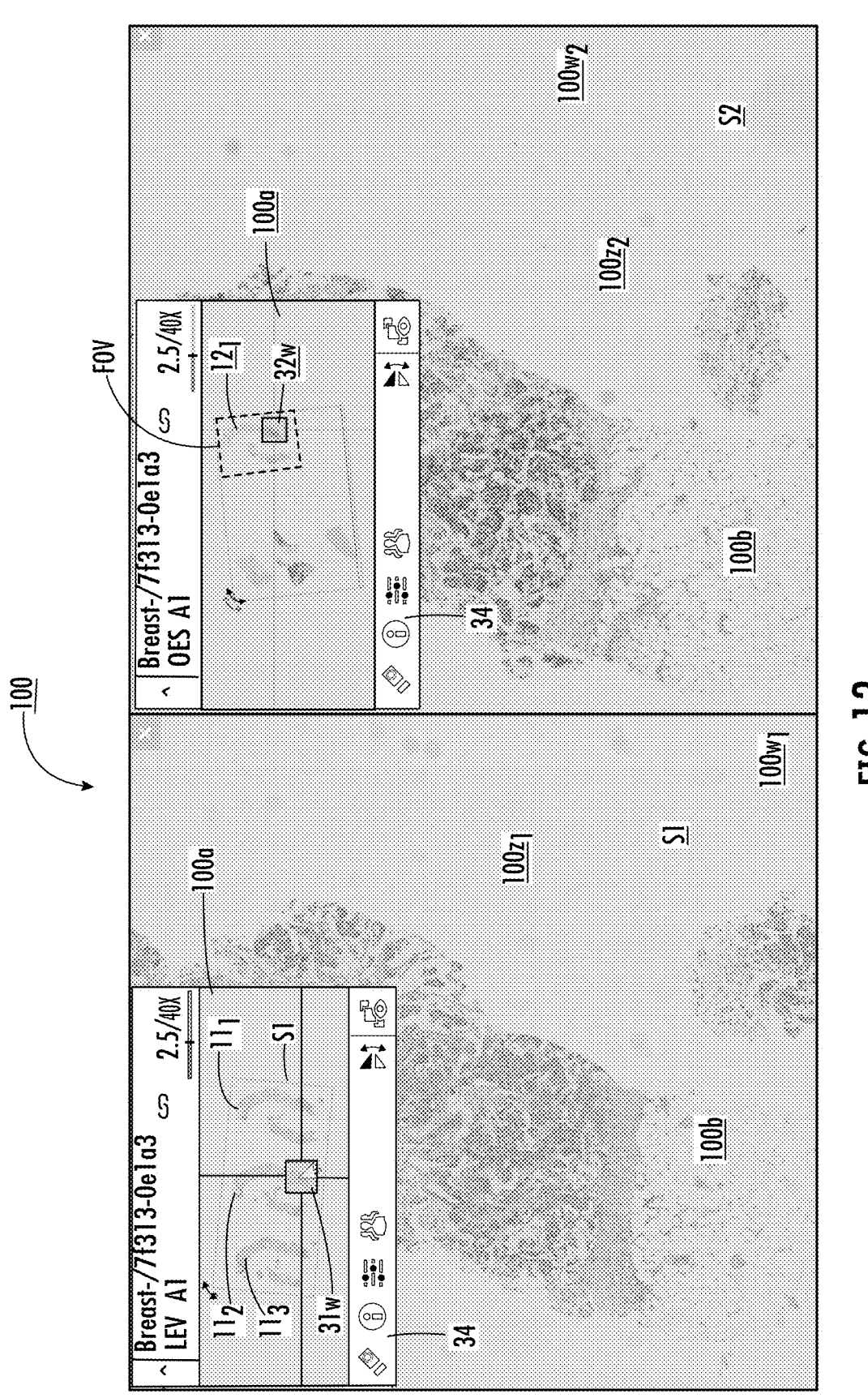
Figure 14:
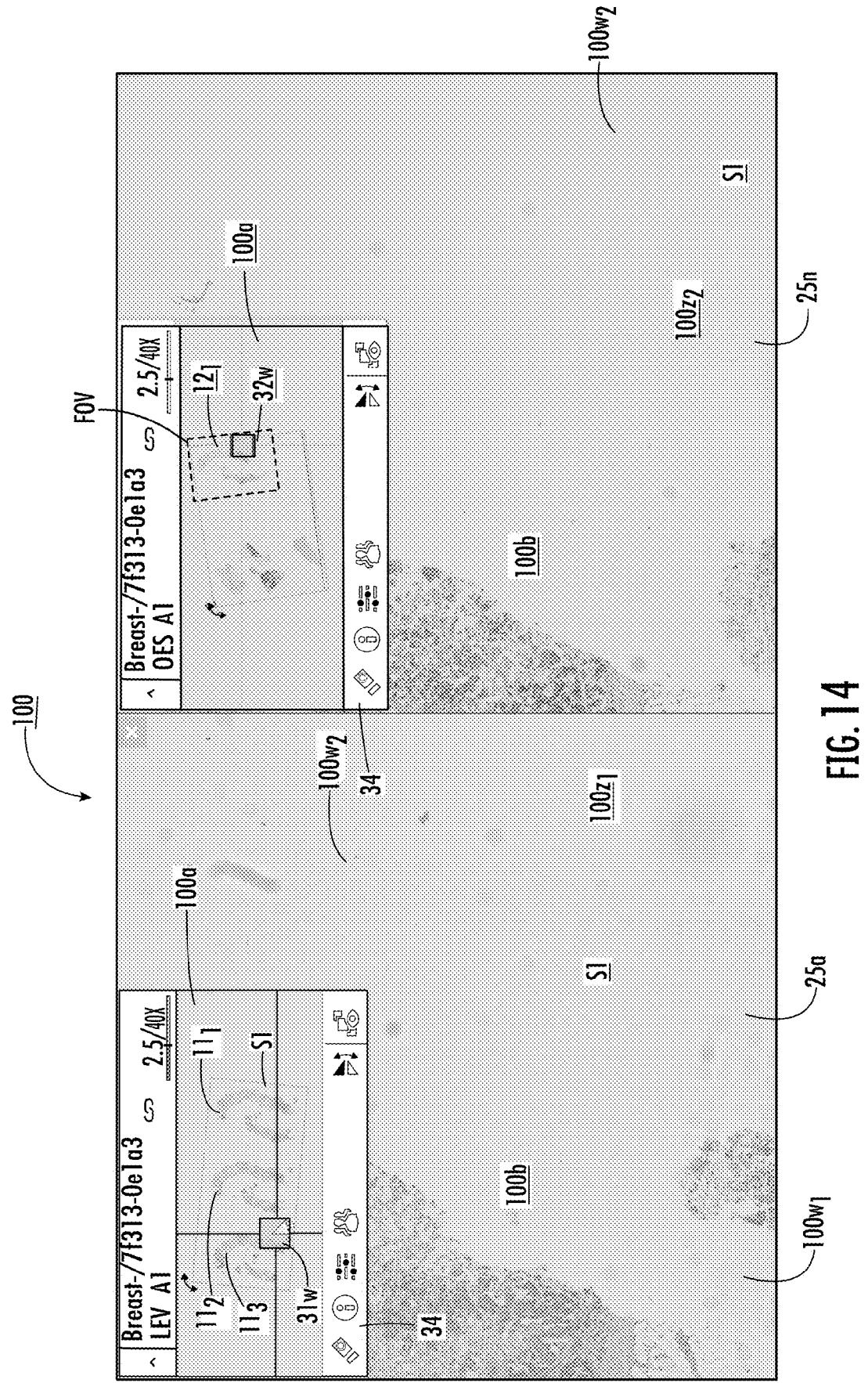

FIGS. 12-14 show a viewer 100 with windows 100w1 and 100w2 providing first and second slides S1, S2, respectively, of tissue from a common tissue block. FIGS. 12-14 show two adjacent slides, S1, S2 provided by a respective window 100w1, 100w2 of the viewer 100. The windows 100w1, 100w2 are configured with first and second viewing sub-windows, 100a, 100b. The first viewing sub-window 100a contains an overview of the full a respective entire slide S1, S2 and can be shown over a portion of the (larger) second viewing sub-window 100b which can provide a respective viewport 100z1, 100z2 containing a zoomed portion of the corresponding slide S1, S2. The viewing sub-window 100a can comprise a set of UI icons 34 for different actions, such as displaying a photo of the entire slide, displaying more detailed information related to the slide, tuning image appearance (brightness, contrast, color), sharing view with collaborators, flipping the image, or toggling review tracking on/off.

The viewer 100 is configured so that one slide S1 or S2 and/or the corresponding whole slide viewing sub-window 100a is active. In this context, "active" means that a user is able to move the viewport (100z1 for S1 or 100z2 for S2, denoted by the outline/box 31w or 32w, respectively) and to navigate to different positions of the slide. The other portion of the viewer 100 provides the other slide, which provides an aligned viewport (100z2 or 100z1, respectively) in response to movement of the viewport, shown using the interface denoted by box 31w or 32w. The user is able to select which of the slides S1 or S2 provided by the viewer 100 is the active slide. The viewer 100 can be a single window that provides both slides S1, S2 or may be two cooperating windows 100w1, 100w2 that each provides a respective slide S1 or S2 with the viewing sub-windows, 100a, 100b.

S1 and S2 can be of tissue from a common tissue block with different stains, such as Haematoxylin and Eosin in the most common staining protocol H&E or an immunohistochemistry stain.

In this example, slide 1, S1, is the active slide 25a whereby a user can move the viewport 100z1 (denoted by the outline 31w) to navigate over and about each of the three spaced apart tissue objects $11_1$, $11_2$, $11_3$, which, in turn, causes the "follower" viewport 100z2 (denoted by the outline 31w) of the second slide S2 to move over and about a single tissue object $12_1$, at least three times, synchronized and in response to, the location of the UI window 30w on each of the three different tissue objects $11_1$, $11_2$, $11_3$ of Slide 1 (S1). It is noted that the medical images, e.g., slides S1, S2, may have a plurality of regions of interest with non-overlapping keypoint clusters (which can be interchangeably described as "landmark clusters" herein) (see, e.g., FIG. 11), rather than spaced apart objects. Thus, the viewport can explore regions rather than just separate objects.

As shown, while slide 2, S2, has several disjointed objects, only the object $12_1$ with the tissue characteristics is explored as the other objects to the left side of the image are not target objects (control piece or other non-relevant object for the registration).

To begin the review, a user can navigate the viewport 100z1 to areas of interest within S1, connected to candidate registrations based on pre-computed data and review of imported slides of the tissue block and all possible registrations, which may optionally use keypoints and "matching" or weighting of keypoints as discussed herein.

A viewer provides respective "windows" 100w1, 100w2, with a GUI whereas the "viewport" 100z1, 100z2 refers to the content displayed in the window including defining a certain area of the image, e.g., WSI.

FIG. 12 illustrates the viewport 100z1 over the first object $11_1$, causing the viewport 100z2 of the second slide S2 to move over the single object $12_1$ at a common, corresponding location of the tissue object irrespective of the tissue object location on the slide S2. At the same time, the respective outlines 31w, 32w also update to reflect the updated viewports of the respective slides S1, S2.

FIG. 13 illustrates the user having moved and zoomed the viewport 100z1 over the second object $11_2$, causing the viewport 100z2 of the second slide S2 to move over the single object $12_1$ at a corresponding location and zoom level of the tissue object $11_2$ irrespective of the tissue object $12_1$ location on the slide S2.

FIG. 14 illustrates the user having moved the viewport 100z1 over the third object $11_3$, causing the viewport 100z2 of the second slide S2 to move over the single object $12_1$ at a corresponding location of the tissue object $11_3$ irrespective of the tissue object $12_1$ location on the slide S2. The registration synchronizing the viewports 100z1, 100z2, is performed automatically and can be based on pre-computed keypoint clusters as described herein.

Thus, the target object $12_1$, here in S2, will be shown again and again independent of what section the user is looking at in the viewport 100z1 of the active view 25a. This is a desired behavior, since the object $12_1$ is here the (only) appropriate immunohistochemistry stain reference to all three H&E-stained objects $11_1$, $11_2$, $11_3$ in S1.

Thus, the user interface (31w or 32w) in the active window causes a user interface of the follower window (the other of 31w or 32w) to move in concert, synchronized to follow movement of the user interface of the active window but restricted to travel only over a field of view (FOV) corresponding to a single region and/or a single object $12_1$ in the non-active window 25n whereby the follower window user interface (here, for example 32w) repeatedly moves about the single region and/or object as the active window user interface (here, for example, 31w) is moved over different regions and/or different ones of spaced apart objects in the active window 25a.

The user interacts with the viewer 100 to navigate the active view 25a, switch the active view 25a to the other slide image, and change one or both of the shown digital images, S1, S2, e.g., WSIs. The viewer 100 can also show more than two slides, and the registration can be applied for more than one non-active slide image, in the same way as for one non-active slide image 25n (slide 2, S2, in FIG. 12).

Embodiments of the invention are directed to user interfaces and associated image processing circuits that provide interactive windows providing a pair of digital image (WSI) slides on a display (typically of a viewer) that can allow a user to electronically navigate using the active view, switch the active view and change the WSIs shown. Pre-computed candidate registrations between the relevant landmarks in the active view 25*a* and their pairings in the synched "moving view"/non-active image 25*n* are fetched (automatically obtained from pre-interrogated and mapped slide data). A candidate registration with the highest quality or weighting is selected. Navigation of the moving view 25*n* is automatically electronically performed according to the selected candidate registration in the active view 25*a*.

Figure 15:
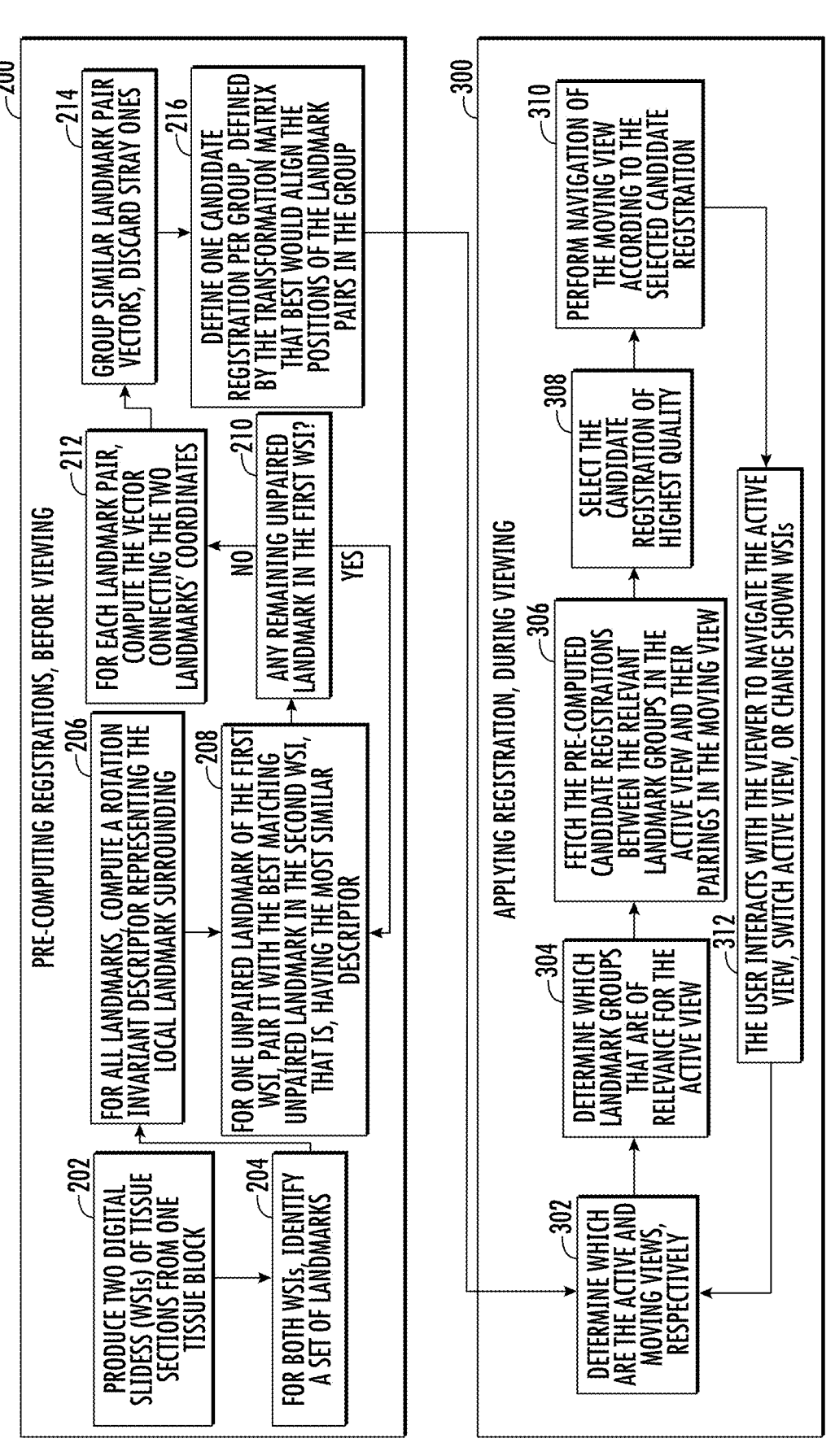
FIG. 15 is a schematic illustration of front-end and back-end modules of an example viewer according to embodiments of the present invention.

Turning now to FIG. 15, a flow chart of example actions that can be used to provide registration between slides of tissue is shown. The flow chart includes two primary cooperating modules, a pre-computing module 200 with a set of actions for identifying candidate registrations before viewing and a viewing module 300 whereby candidate registrations are provided.

Two digital slides (WSIs) of tissue sections from one tissue block are provided (block 202). For both WSIs, identify a set of landmarks (block 204). For all landmarks, compute a rotation invariant descriptor representing the local landmark surrounding (block 206). For one unpaired landmark of the first WSI, pair it with the best matching unpaired landmark in the second WSI, that is, having the most similar descriptor (block 208).

Any remaining unpaired landmark in the first WSI? (block 210). If yes, repeat (block 208). If no, for each landmark pair, compute the vector connecting the two landmarks' coordinates (block 212). Group similar landmark pair vectors, discard stray ones (block 214). Define one candidate registration per group, defined by the transformation matrix that best aligns the positions of the landmark pairs in the group (block 216).

For the viewing module 300, determine which are the active and moving views, respectively (block 302). Determine which keypoint groups/landmark groups that are of relevance for the active view (block 304). Fetch the pre-computed candidate registrations between the relevant landmark groups in the active view and their pairings in the moving view (block 306). Select the candidate registration of highest candidate registration quality measure (block 308). As discussed further below, the term "highest quality" for the candidate registration quality measure(s) can refer to the highest number of keypoints in the respective relevant keypoint groups (landmark groups) or other defined criteria ranking quality. Electronically, automatically navigate the moving view according to the selected candidate registration (block 310). The user interacts with the viewer to navigate the active view, switch active view, or change shown WSIs (block 312).

As part of the method to execute a registration, candidate registration quality measures can be used to compare candidate registrations are employed. Such quality measures can be implemented in many ways. A primary way to define such a quality measure is as the number of keypoint pairs (or sets) in the respective candidate registration, where a larger number corresponds to higher quality, as it can be expected to yield a more precise mapping between the two images. Another possible candidate registration quality measure, or component of a quality measure, is the variation of keypoint pair vectors in the cluster defining the candidate registration (for instance measured by standard deviation), where lower variation means higher quality. Yet another possible quality measure, or component of a quality measure, is the aggregated difference between the paired keypoint descriptors across the cluster defining the candidate registration (for instance measured by Euclidian distance), where smaller difference means higher quality. Combinations of the above and/or further quality measures or components of candidate regsitration quality measures are also possible.

The method has been evaluated on a tissue stratified random sample from 5 histology labs, on 243 pairs of images, with the correct registration being among the found registrations in 77% of the cases based on the user-selected registration protocol.

Figure 7:
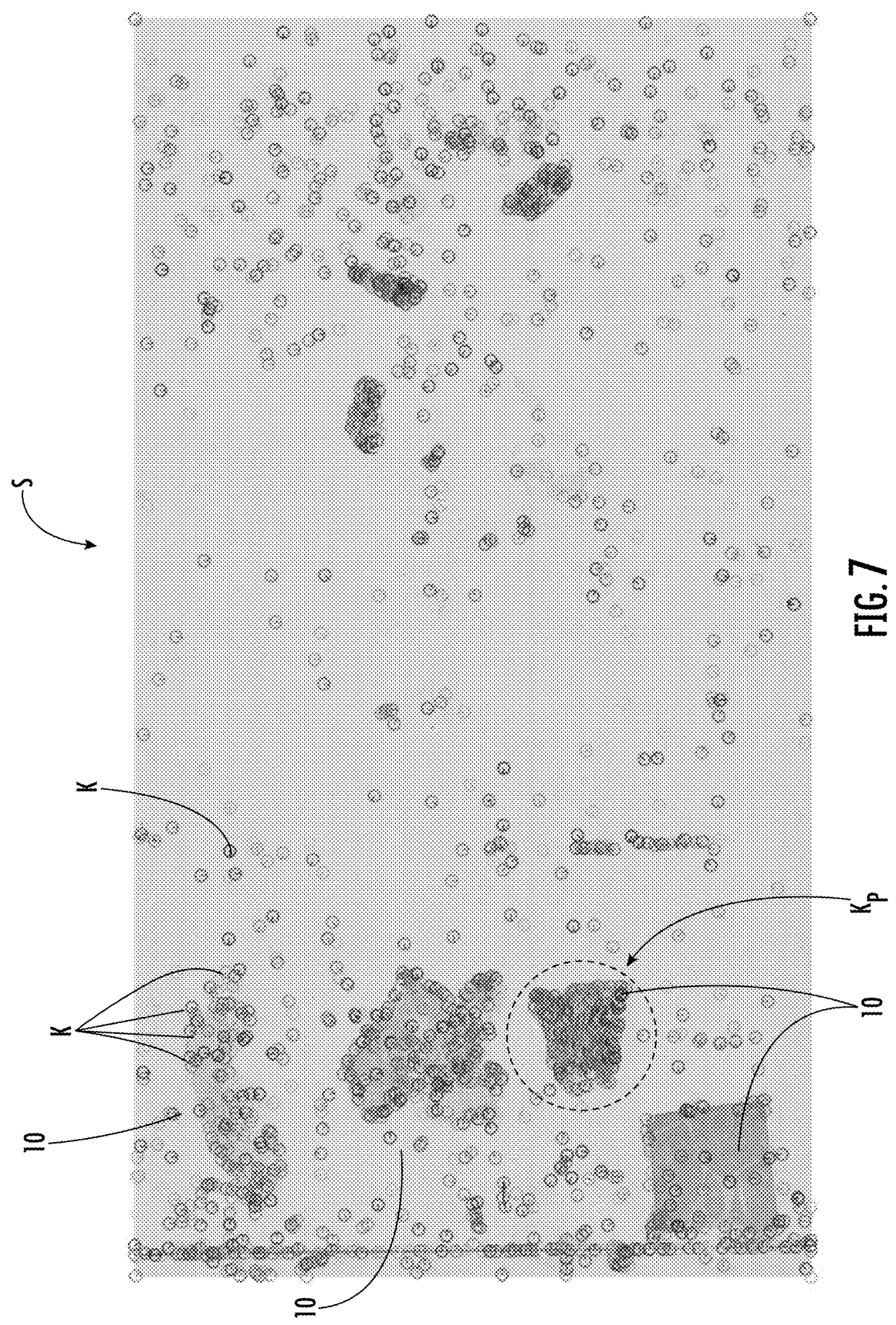
FIG. 7 an image of a pathology slide with electronic circles representing key points positioned over various tissue pieces according to embodiments of the present invention.

Turning now to FIG. 7, in an example implementation of the candidate registration process, a keypoint detector can be used to find high contrast keypoints K and a rotation invariant descriptor is calculated/defined for each keypoint K. Different numbers of keypoints K can be used in different embodiments of the invention. FIG. 7 shows detected keypoints K in a digital pathology slide S.

The keypoint detection is a feature identification process that can be performed automatically and electronically. See, e.g., Ma, J., Jiang, X., Fan, A. et al. Image Matching from Handcrafted to Deep Features: A Survey. Int J Comput Vis 129, 23-79 (2021), the content of which is hereby incorporated by reference herein.

The choice to base the registration process on identified keypoints is very suitable for pathology images since the calculated key points in the control pieces and in image artifacts can be filtered out during the matching process. Also, the key point registration algorithms can be scale invariant for some uses, for example, registering two photographic images. This can be turned off for pathology images by turning off the scale invariancy of the descriptor, since the scale is known in pathology images.

Figure 16:
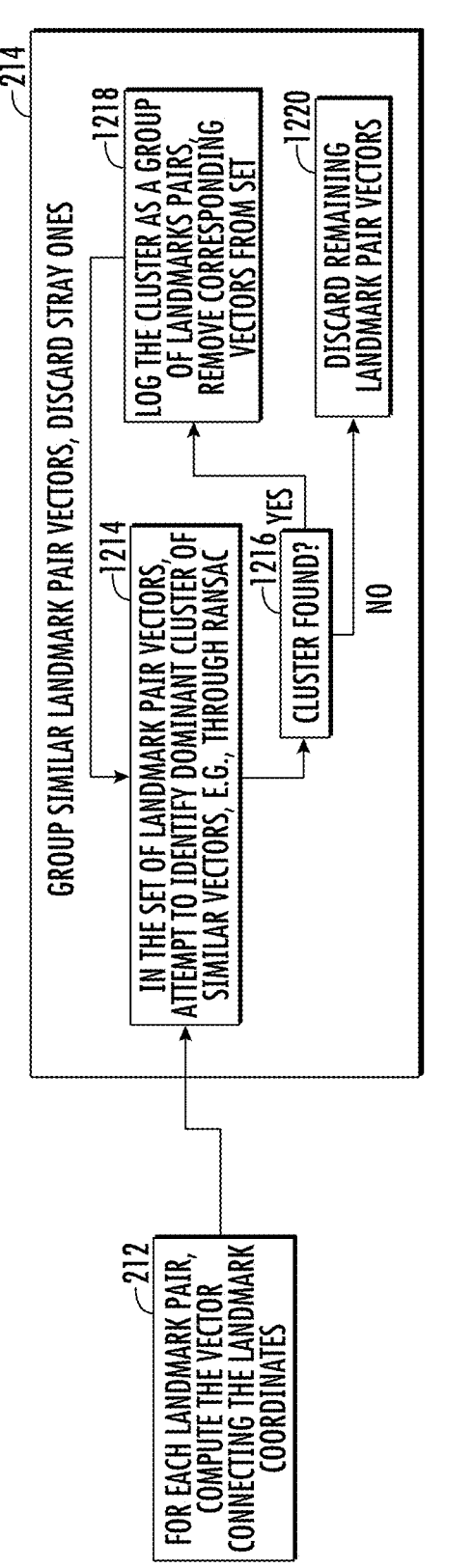
FIG. 16 is a flow chart of actions that can be carried out to group landmark pair vectors for the back-end module shown in FIG. 15.

Turning now to FIG. 16, an example set of actions for the grouping of landmark pair vectors (block 214) of the candidate registration process is shown. For each landmark pair, compute the vector connecting the landmark coordinates (block 212). For (block 214, FIG. 15), in the set of landmark pair vectors, attempt to identify dominant cluster of similar vectors, e.g., through RANSAC (see, M. A. Fischler and R. C. Bolles. Random sample consensus: A paradigm for model fitting with applications to image analysis and automated cartography. Communications of the ACM, 1981, the contents of which are hereby incorporated in full herein) (block 1214). Determine if a cluster is found (block 1216). If yes, log the cluster as a group of landmarks pairs, remove corresponding vectors from set (block 1218) and repeat the cluster identification on the reduced set (block 1214). If no, discard remaining landmark pair vectors (block 1220).

In the example provided in FIGS. 9-10, the first landmark pair cluster (corresponding to a candidate registration) is on the left (FIGS. 9A & 10A), the second landmark pair cluster/candidate registration is on the right (FIGS. 9B & 10B) and the third landmark pair cluster/candidate registration is between the first and second cluster (FIGS. 9C & 10C).

Only candidate registrations with enough keypoints are kept for use in the registration process, using an experimental and/or defined threshold. The candidate registrations can be performed during image import, incrementally when new slide images are added to a corresponding slide block of related tissue of a patient in the database.

Figure 11:
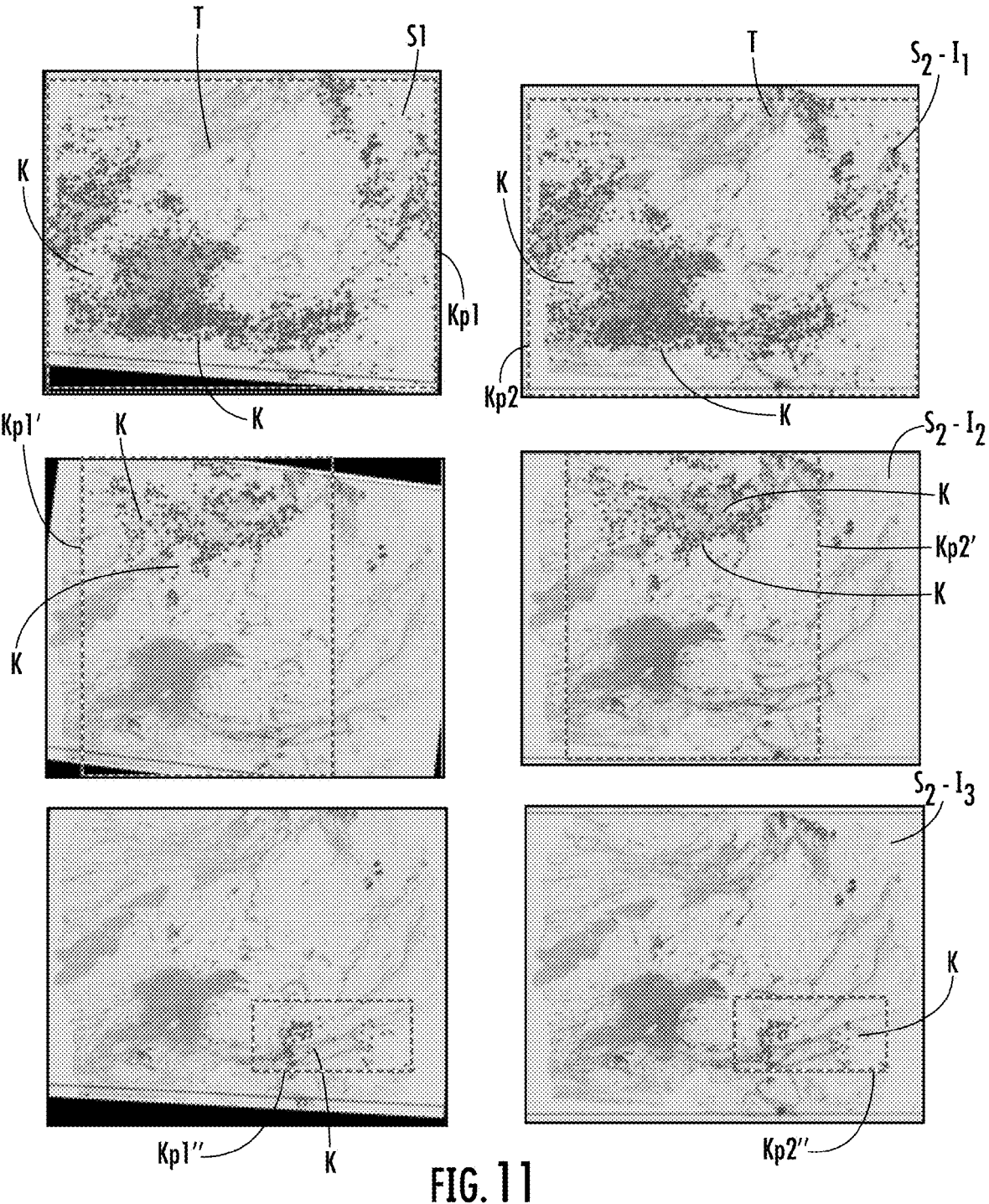
FIG. 11 shows two slides with three candidate registrations (represented by keypoint groups) with similar, but different mappings that may be identified by a viewer when a viewport covers more than one possible registration according to embodiments of the present invention.

Now turning to FIG. 11, showing an example of a coherent piece of tissue T being connected to several landmark pair clusters. This can happen due to slight spatial distortion of the tissue section during lab preparation, such as shearing or introducing creases or folds. In this case, the first cluster identified (FIG. 16, block 1214), dominant in terms of the largest number of keypoints for keypoint cluster pairs Kp1, Kp2, is shown in the top two images. The second cluster Kp1', Kp2' (repeating block 1214 in FIG. 16) is shown in the middle row of images and the third cluster Kp1", Kp2" (repeating block 1214 in FIG. 16) is shown in the bottom row. The three different clusters represent slightly different candidate registrations.

A number of keypoints K can be associated with a respective "region" in an image. That is, a region refers to an area spanned by a set of keypoints K, e.g., the keypoint clusters Kp1 or Kp2, for example.

As shown in FIG. 11, there are three candidate registrations between the slides S1-S2 but the mappings between the three registrations are very similar The first iteration, S2-I1, top candidate registration, has the largest number of cluster keypoints Kp1, Kp2 (shown as clusters of blue dots). Typically, one landmark equals one keypoint in example embodiments. The middle candidate registration, second iteration S2-I2, uses only keypoints Kp1', Kp2' in a top portion of the images with the first iteration S2-I1, top candidate registration keypoints Kp1, Kp2 removed. The bottom candidate registration, third iteration S2-I3, uses only keypoints Kp1", Kp2" in a bottom, right of the images with the keypoints of the first iteration S2-I1 and S2-I2 second iteration removed. This iterative "starvation" of keypoints entails that later identified clusters of keypoints are generated from a smaller set of keypoints K compared to earlier identified clusters.

It is noted that "keypoints" and "landmarks" are used interchangeably herein to indicate common features of potential relevance for potential registration between medical images. Different image regions can have different numbers of keypoints and different arrangements of keypoints (or landmarks, where one keypoint is one landmark).

The starvation of keypoints also occurs when one area of a first slide can be mapped to several areas of a second slide, as shown in FIGS. 9A-9C (one area, first slide) and the corresponding candidate registrations to the three areas in the second slide in FIGS. 10A-10C. Having too few keypoints left could mean that relevant clusters are not identified or that their entailing registration becomes imprecise. One effective mitigation of that risk is to have a large number of keypoints to begin with, where about a 100-1000 keypoints has been found to be effective but the method allows increasing up to 10,000 or more keypoints as well. Good registration quality is typically achieved if a cluster has at least 30 keypoints, but down to about 10 keypoints per cluster may be effective as well.

Again referring to FIG. 11, the three candidate registrations for the same piece of tissue may be seen as "duplicates". Instead of filtering such duplicates out, it is better to keep them since can allow for registration for deformations and breaks in the tissue, which is very common. Selection of the candidate registration to apply can be based on the viewport proximity to the midpoint of the landmark clusters connected to the candidate registrations. Such an approach may, however, cause unwanted abrupt navigation jumps in the non-active view when the selected candidate registration changes. Therefore, to ensure smooth navigation, the performed registration can be based on interpolation of two or more candidate registrations based on their relative proximity to the viewport midpoint.

Such an interpolation scheme is described in the flow chart of FIG. 18. In other words, the candidate registration quality measure can be calculated using weighted criteria to provide a range of high to low candidate registration quality measures. A weighted combination of candidate registrations can be used as an alternative to a quality measure of a single respective candidate registration. For example, weights for each relevant keypoint group/landmark group/set in the active view are calculated, based on the distance from the respective group's center of mass to the viewport midpoint (block 307). Perform navigation of the moving view according to an interpolation of the selected candidate registrations, using the computed weights (block 311). The user interacts with the viewer to navigate the active view, switch active view, or change shown WSIs (block 312). It is noted that in addition to distances, the interpolation weights can also incorporate the quality measures discussed above or be solely based on the quality measures.

Figure 17:
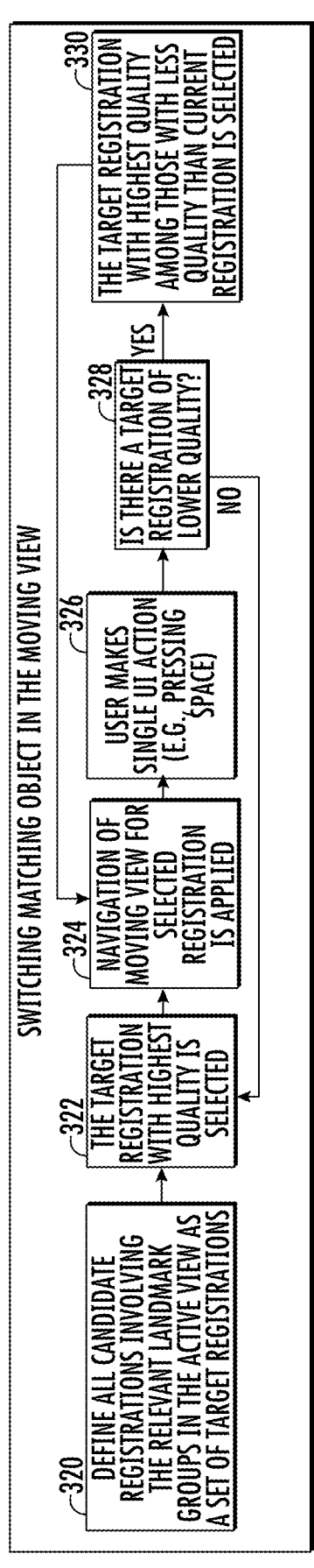
FIG. 17 is a flow chart of actions that can be used by the front-end module to provide a switch of matching object in a moving view of a viewer according to embodiments of the present invention.

Referring to FIG. 17, an example flow chart for "clutching" actions are shown for switching matching region(s) and/or object(s) in the moving view. The flow chart refers to situations like the one exemplified in FIGS. 8-10, where clutching refers to keeping the active view 25*a* (slide S1) still while jumping between several relevant candidate registrations in the non-active view 25*n* (slide S2). First, define all candidate registrations involving the relevant landmark groups in the active view as a set of target registrations (block 320). The target registration with highest quality is selected (block 322). Navigation of moving view for selected registration is applied (block 324). User makes single UI action (e.g., pressing space) (block 326). Is there a target registration of lower quality? (block 328). If yes, the target registration with highest quality among those with less quality than current registration is selected and navigation of moving view for selected registration is applied (block 330). If no, the target registration with highest quality is selected (322) and the next sequence of steps repeated.

Figure 19:
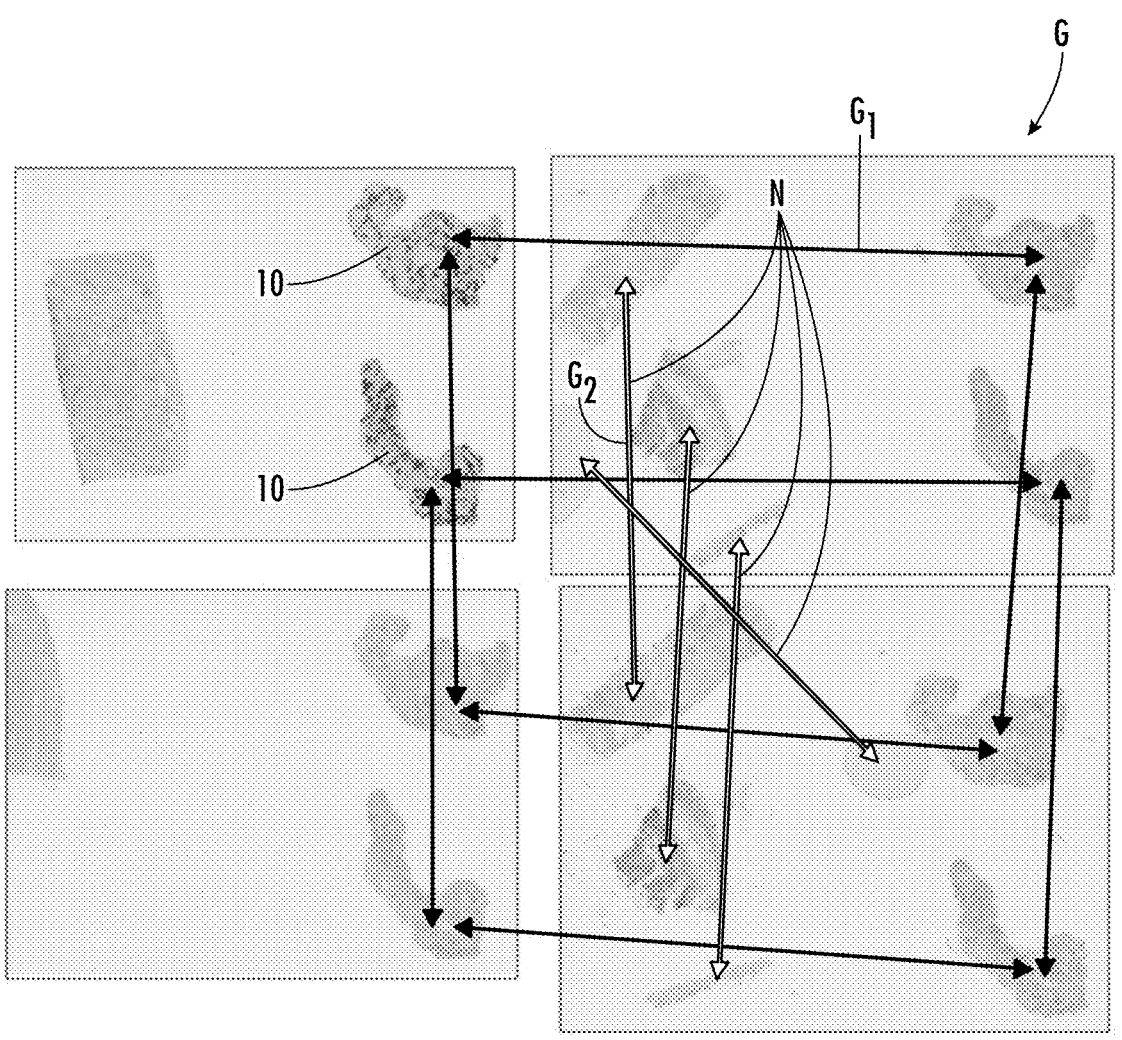
FIG. 19 is a schematic illustration of connectivity/lack of connectivity features of slides and tissue pieces used to identify whether a slide has a tissue piece under investigation by a user according to embodiments of the present invention.

FIG. 19 is a schematic illustration of a candidate registration method that can be used on tissue blocks from which three or more slides S have been produced. The registrations between slides S can create a graph structure G with graph lines G1, G2 between pieces of tissue 10. This graph can be used to filter out pieces of tissue. Since the control piece is most commonly specific to the staining used, it will typically not be present in all slides. Thus, pieces that do not have a connection to most slides, e.g., graph lines G2, are probably not N the tissue under investigation. Here, the G2 lines with arrows are not connected to all slides and pieces 10 connect to these arrows G2 are probably safely excluded as a piece under investigation.

Figure 20:
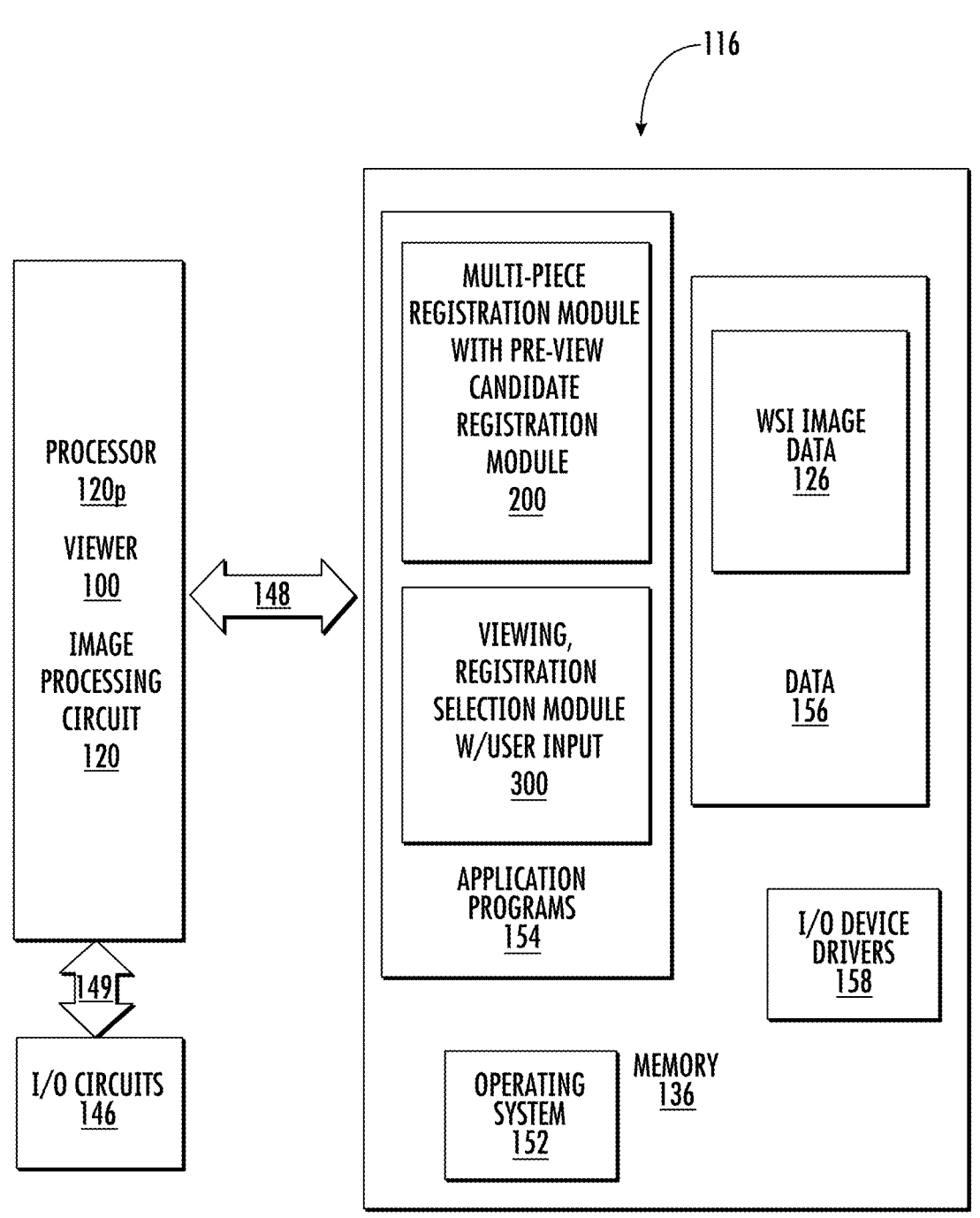
FIG. 20 is a schematic illustration of a data processing circuit according to some embodiments of the present invention.

As illustrated in FIG. 20, embodiments of the invention may be configured as a data processing system 116, which can include a (one or more) processors 120*p,* a memory 136 and input/output circuits 146. The one or more processors 120*p* can be part of a viewer 100 and/or imaging processing circuit 120. The data processing system may be incorporated in, for example, one or more of a personal computer, database, workstation W, server, router or the like. The data processing system 116 can reside on one machine or be distributed over a plurality of machines. The processor 120*p* communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

In particular, the processor 120p can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: ROM, PROM, EPROM, EEPROM, flash memory, SRAM, DRAM and magnetic disk. In some embodiments of the present invention, the memory 136 may be a content addressable memory (CAM).

As further illustrated in FIG. 20, the memory (and/or storage media) 136 may include several categories of software and data used in the data processing system: an operating system 152; application programs 154; input/output device drivers 158; and data 156. As will be appreciated by those of skill in the art, the operating system 152 may be any operating system suitable for use with a data processing system, such as MS-Windows, Mac OS, iOS, Android OS, Ubuntu, Fedora, Solaris, Free BSD, Chrome OS, CentOS, Debian, Deepin, IBM®, OS/2®, AIX® or zOS® operating systems or Microsoft® Windows®95, Windows98, Windows2000 or WindowsXP operating systems, Unix or Linux™, IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154 the operating system 152 the input/output device drivers 158 and other software programs that may reside in the memory 136.

The data 156 may include (archived or stored) digital image data sets of tissue blocks 126 correlated to respective patients. As further illustrated in FIG. 20, according to some embodiments of the present invention, the application programs 154 include a multipiece digital slide image registration Module 200 configured to provide a pre-view set of candidate registrations for tissue slides of a tissue block of a patient and a viewing, registration selection module with user input Module 300. The application program 154 may be located in a local server (or processor) and/or database or a remote server (or processor) and/or database, or combinations of local and remote databases and/or servers.

While the present invention is illustrated with reference to the application programs 154, and Modules 200, 300 in FIG. 20, as will be appreciated by those of skill in the art, other configurations fall within the scope of the present invention. For example, rather than being application programs 154 these circuits and modules may also be incorporated into the operating system 152 or other such logical division of the data processing system. Furthermore, while the application programs 200, 300 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 20 but may be provided by other arrangements and/or divisions of functions between data processing systems. For example, although FIG. 20 is illustrated as having various circuits and modules, one or more of these circuits or modules may be combined or separated without departing from the scope of the present invention.

Figure 21:
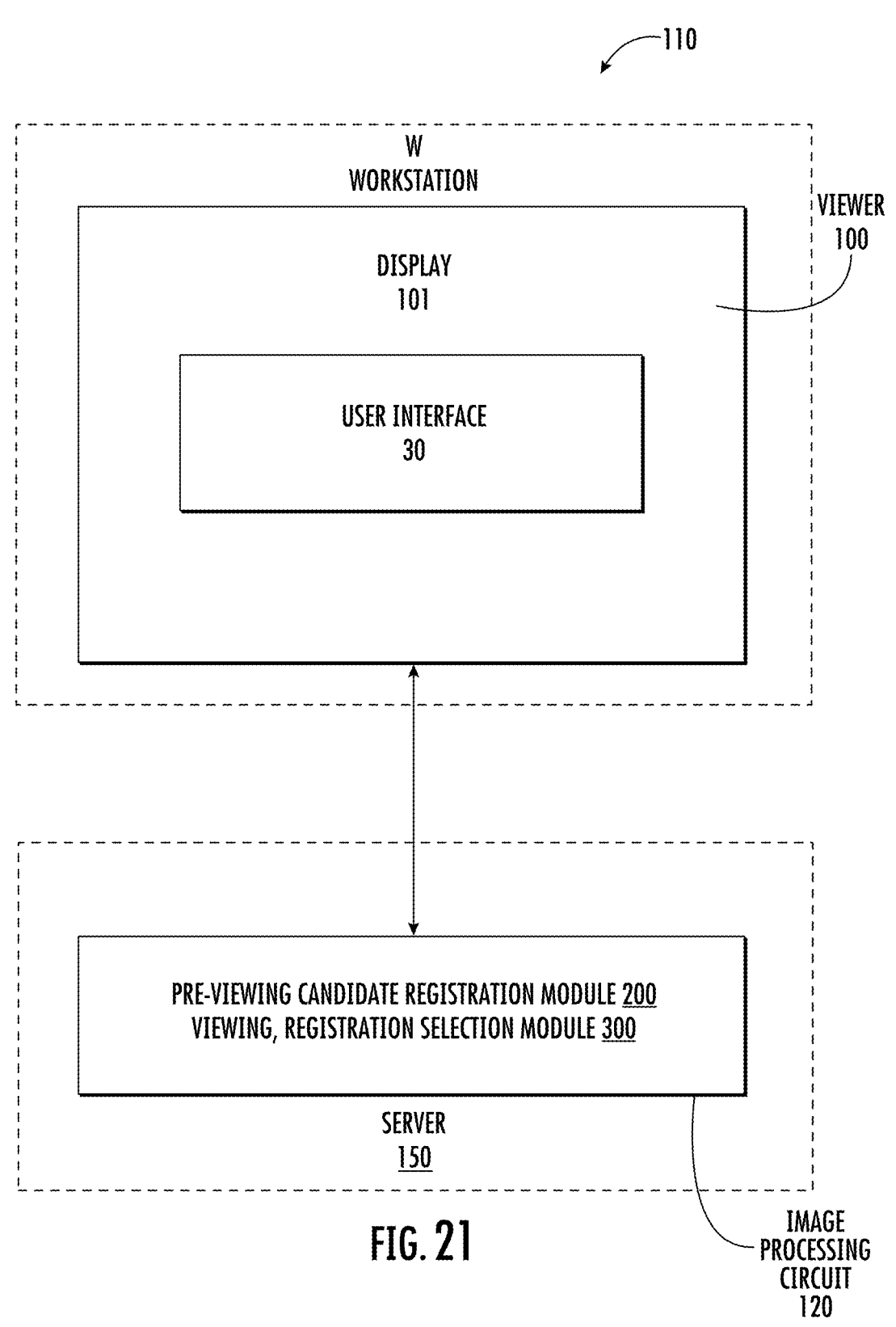
FIG. 21 is an example of workstation with a viewer providing a display screen with user-interactive window(s) according to embodiments of the present invention.

FIG. 21 shows a viewer system 110 with a workstation W providing display 101 with a viewer 100 and user interface 30. The workstation W can comprise an image processing circuit or be in communication with a server 150 that is configured to provide at least part of the image processing circuit 120. The image processing circuit 120 can comprise the pre-viewing module 200 and the viewing module 300 and can be configured to generate the pre-viewing data with the possible candidate registrations for presentation to a user upon selection of a region and/or object in an image in an active view of a viewport.

The image processing circuit 120 can include one or more processors 120p and can be partially or totally held in the workstation W with the display 101 or may be partially or totally remote from a workstation, such as held in one or more servers 150 and accessible via the Internet via firewalls. The one or more servers 150 can be integrated into a single server or may be distributed into one or more servers or other circuits or databases at a single physical site or at spatially separate locations. Similarly, the modules 200, 300 can be held by the one or more servers 150 and/or can be distributed into multiple processors or databases or integrated into one.

The server 150 may be embodied as a standalone server or may be contained as part of other computing infrastructures. The server 150 may be embodied as one or more enterprise, application, personal, pervasive and/or embedded computer systems that may be standalone or interconnected by a public and/or private, real and/or virtual, wired and/or wireless network including the Internet, and may include various types of tangible, non-transitory computer-readable media. The server 150 may also communicate with the network via wired or wireless connections, and may include various types of tangible, non-transitory computer-readable media.

The server 150 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser) and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

Users can communicate with the server 150 via a computer network, such as one or more of local area networks (LAN), wide area networks (WAN) and can include a private intranet and/or the public Internet (also known as the World Wide Web or "the web" or "the Internet." The server 150 can include and/or be in communication with modules 200, 300 using appropriate firewalls for HIPPA or other regulatory compliance.

Embodiments of the present invention may take the form of an entirely software embodiment or an embodiment combining software and hardware aspects, all generally referred to herein as a "circuit" or "module." Furthermore, the present invention may take the form of a computer program product on a (non-transient) computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation) computer, partly on one computer, as a stand-alone software package, partly on the workstation's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of registering medical images for viewing, comprising:

electronically providing a database of candidate registrations of a plurality of different medical images for respective patients, wherein a pair of the different medical images of a single patient of the plurality of different medical images has multiple candidate registrations in the database of candidate registrations, and wherein multiple image regions of a first medical image of the pair of the different medical images are each related to an image region in a second medical image of the pair of different medical images through at least one candidate registration in the database of candidate registrations;

electronically providing a viewer comprising a first window with a first viewing window user interface and a second window with a second viewing window user interface;

displaying a viewport of the first medical image in the first window;

displaying a viewport of the second medical image in the second window;

accepting user input of a user to select one of the first window or the second window to be an active window for user navigation and which makes a non-selected other of the first window or the second window a non-active, follower window;

obtaining candidate registrations from the database of candidate registrations that are related to the first medical image or the second medical image in the active window; and electronically automatically selecting a registration from the obtained candidate registrations based on proximity of the image region of the obtained candidate registrations to the viewport of the active window, wherein each image region is an area that is defined by a respective keypoint cluster, and wherein the electronically automatically selecting a registration from the obtained candidate registrations is based on a candidate registration quality measure.

2. The method of claim 1, wherein each candidate registration in the database of candidate registrations has a respective candidate registration quality measure.

3. The method of claim 1, wherein the candidate registrations in the database of candidate registrations are computed through keypoint pairing of pairs of first and second keypoint clusters, the first keypoint cluster in the first medical image and the second keypoint cluster in the second medical image.

4. The method of claim 1, wherein the candidate registration quality measure is calculated based, at least in part, by a number of keypoints in a respective keypoint cluster, with keypoint clusters having a greatest number correlated to a greater registration quality measure.

5. The method of claim 1, wherein the selecting comprises determining viewport proximity of the first or second viewport that is the active window to a midpoint of keypoint clusters connected to the candidate registrations.

6. The method of claim 1, further comprising automatically electronically moving the viewport of the follower window according to the selected registration whereby the viewport of the first medical image and the viewport of the second medical display respective, corresponding image portions of the first and second medical images.

7. The method of claim 1, further comprising:

changing the viewport of the active window as directed by the user in a user interface of the active viewing window to navigate about image regions in the active window; then, in response to change of the viewport of the active window, automatically electronically moving the viewport of the follower window, synchronized to follow movement of the viewport of the active window.

8. The method of claim 1, further comprising accepting user input to change the viewport of the active window and automatically electronically repeating the selecting registration step and automatically moving the viewport of the follower window according to the change in the viewport of the active window.

9. The method of claim 8, further comprising changing one or more selected registrations from the obtained candidate registrations whereby different objects in the image region of the active window becomes aligned with a common (the same) region in the image region of the follower window.

10. The method of claim 1, wherein the medical images are digital pathology slide images of a tissue block of the single patient.

11. The method of claim 1, wherein keypoints of spaced apart objects in different image regions are used to identify similar objects in the different medical images to identify candidate registrations for the obtaining step.

12. The method of claim 1, further comprising electronically determining if there are candidate registrations that have an image region overlapping with the viewport in the active window and accepting user input via a single user interface action, whereby each single user interface action executes selection of another candidate registration in the order of decreasing candidate registration quality measure.

13. The method of claim 12, wherein a sequence of selecting candidate registrations in response to respective single user interface actions is ordered according to spatial location of the image region of the non-active window with the image region of the candidate registrations.

14. The method of claim 1, wherein the selected registration is carried out, at least in part, by selecting a plurality of different candidate registrations from the obtained candidate registrations corresponding to a current position of the active image viewport, wherein each of the selected plurality of candidate registrations corresponds to a different relevant image region in the active image.

15. The method of claim 14, wherein each of the selected plurality of candidate registrations has a weighting used for the candidate registration quality measure, and wherein the weighting is based on a distance from a center of mass of an active image keypoint cluster in a respective selected candidate registration to centerpoint of the active image viewport.

16. A viewer system for evaluating Whole Slide Images (WSI), comprising:

a display; and a circuit in communication with the display, the circuit comprising at least one processor that:

provides or in communication with a database of candidate registrations of a plurality of different medical images for respective patients, wherein a pair of the different medical images of a single patient of the plurality of different medical images has multiple candidate registrations in the database of candidate registrations, wherein each region of multiple regions of a first medical image of the pair of the different medical images is related to a region in a second medical image of the pair of different medical images through at least one candidate registration in the database of candidate registrations;

provides a viewer comprising a first window and a second window;

displays a viewport of the first medical image in the first window;

displays a viewport of the second medical image in the second window;

accepts user input of a user to select one of the first window or the second window to be an active window for user navigation and which makes a non-selected other of the first window or the second window a non-active, follower window;

obtains candidate registrations from the database of candidate registrations that are related to the first medical image or the second medical image in the active window; and selects a registration from the obtained candidate registrations based on proximity of the image region of the obtained candidate registration to the viewport of the active window, wherein each image region is an area that is defined by a respective keypoint cluster, and wherein the obtained candidate registrations are based on candidate registration quality measures.

17. The viewer system of claim 16, wherein an image region is associated with an area spanned by keypoint clusters.

18. The viewer system of claim 16, and wherein each candidate registration in the database of candidate registrations has a respective candidate registration quality measure.

19. The viewer system of claim 18, wherein the at least one processor is configured to:

determine if there are candidate registrations that have an image region overlapping with the viewport in the active window; and accept user input via a single user interface action, where each action executes selection of another candidate registration in the order of decreasing candidate registration quality measure.

20. The viewer system of claim 16, wherein the at least one processor is configured to automatically move the viewport of the follower window according to the selected registration whereby the viewport of the first medical image and the viewport of the second medical display respective, corresponding image portions of the first and second medical images.

21. The viewer system of claim 16, wherein the at least one processor is further configured to:

change the viewport of the active window as directed by the user in a user interface of the active viewing window to navigate about image regions in the active window; then, in response to change of the viewport of the active window, automatically move the viewport of the follower window, synchronized to follow movement of the viewport of the active window.

22. The viewer system of claim 16, wherein the circuit is configured to accept user input to change the viewport of the active window whereby the at least one processor then automatically selects another candidate registration as a current selected registration and moves the viewport of the follower window according to the change in the viewport.

23. The viewer system of claim 16, wherein the at least one processor is configured to provide a sequence of selecting candidate registrations in response to user action that is ordered according to spatial location of the image region of the non-active window with the image region of the candidate registrations.

24. The viewer system of claim 16, wherein the selected registration is carried out, at least in part, by selecting a plurality of candidate registrations corresponding to a position of the active image viewport, each selected plurality of candidate registrations corresponds to a different relevant image region in the active image.

* * * * *